(12) United States Patent
Sorge et al.

(10) Patent No.: US 6,627,436 B2
(45) Date of Patent: *Sep. 30, 2003

(54) VECTOR FOR GENE EXPRESSION IN PROKARYOTIC AND EUKARYOTIC SYSTEMS

(75) Inventors: Joseph A. Sorge, Wilson, WY (US); Kerstien A. Padgett, San Diego, CA (US)

(73) Assignee: Stratagene, LaJolla, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/961,888

(22) Filed: Oct. 31, 1997

(65) Prior Publication Data

US 2001/0016351 A1 Aug. 23, 2001

(51) Int. Cl.$^7$ ................................................ C12N 15/63
(52) U.S. Cl. .................................... 435/320.1; 536/24.1
(58) Field of Search ............................... 435/69.1, 69.7, 435/9.41, 320.1; 536/23.4, 23.5, 24.1

(56) References Cited

U.S. PATENT DOCUMENTS 5,266,490 A    11/1993  Davis et al.

OTHER PUBLICATIONS

Zheng et al. A new expression vector for high level protein production, one step purification and direct isotopic labeling of calmodulin–binding peptide fusion proteins. Gene vol. 186 pp. 55–60, 1977.*
Petty. Metal chelate affinity chromatography, In Current Protocols in Molecular Biology (Ausubel et al. Eds.) pp. 10.11.10–10.11.24, John Wiley & Sons, New York, 1996.*
Mertens et al. Versatile, multi–featured plasmids for high–level expression of heterologous genes in *Escherichia coli*: overproduction of human and murine cytokines. Gene vol. 164 pp. 9–15, 1995.*
Beckwith, The lactose operon. In *Escherichia coli* and *Salmonella typhimurium* Cellular and Molecular Biology (Neidhardt et al. Eds.) pp. 1444–1452 Amer. Soc. Microbiol. Wash. D.C., 1987.*
Lusky et al. Inhibition of SV40 replication in simian cells by specific pBR322 DNA sequences. Nature vol. 293 pp. 79–81, 1981.*
Aruffo, Transient expression of proteins using COS cells. In Current Protocols in Molecular Biology (Ausubel et al. Eds.) pp. 16.13.1–16–13–7 John Wiley & Sons, New York, 1998.*
He et al. Phage RNA polymerase vectors that allow efficient gene expression in both prokaryotic and eukaryotic cells. Gene vol. 164 pp. 75–79, 1995.*
Stratagene Catalog Stratagene Cloning Systems p. 27, 1994.*
Padgett et al. Creating seamless junctions independent of restriction sites in PCR cloning. Gene vol. 168 pp. 31–35, 1996.*
He, Biao et al., 1995, *Gene* 164:75–79.
Mole, S.E., 1987, *Nucl. Acids Res* 15: 9090.
Manoharan, H.T. et al., 1997, *Gene* 193:229–237.
MacGregor, G.R. et al., 1989, *Nucl. Acids Res.* 17:2365.
Watanabe et al., 1987, *J. Biol. Chem.* 262:4812–4818.
Wu, et al., 1991, *Molec. Cell Biol.* 11: 4423–4430.
Azuma et al., 1992, *J. Biol. Chem.* 267: 1609–1614.
Fraser et al., 1989, *Molec. Pharmacol.* 36: 840–847.
Bonner, 1989, *Trends Neurosci.* 12: 148–151.
Shine, J., et al. 1974, *Proc. Natl. Acad. Sci.* 71:1342–1346.
Kozak, M. 1986, *Cell* 44:283–292.
Padgett, K. A. et al., 1996, *Gene* 168:31–35.
Padgett, K. A. et., *Strategies* 9:14–16 (1996).

* cited by examiner

*Primary Examiner*—John S. Brusca
(74) *Attorney, Agent, or Firm*—Kathleen M. Williams; Palmer & Dodge, LLP

(57) ABSTRACT

The invention concerns an expression vector that permits expression of genes and fragments thereof in both prokaryotic and mammalian systems. The invention also pertains to derivatives of such vector that contain one or more prokaryotic or eukaryotic (especially mammalian) genes or gene fragments. The invention further pertains to prokaryotic or mammalian cells containing such an expression vector or derivative.

1 Claim, 3 Drawing Sheets

```
RhCM    ................GCGGTAGGCGTGCCT--ATGGGCGGTCTATATAA
AgMCMV  ................GCGGTAGGCGTGCCTAATGGGGAGGTCTATATAA
hCMV    CCCCATTGACGCAAATGGGGCGGTAGGCGTGTACGGTGGGGAGGTCTATATAA araBAD  CTGACG                                    TACTGT        ⇑
        TTGACA                                    TATAAT    mapped
        -35 consensus                             -10 consensus  transcription
        region                                    region    start site
```

FIG. 3

SEQUENCE LISTING (1) GENERAL INFORMATION:

(iii) NUMBER OF SEQUENCES: 40

(2) INFORMATION FOR SEQ ID NO:1:

(i) SEQUENCE CHARACTERISTICS:
      (A) LENGTH: 32 base pairs
      (B) TYPE: nucleic acid
      (C) STRANDEDNESS: single
      (D) TOPOLOGY: linear (xi) SEQUENCE DESCRIPTION: SEQ ID NO:1:

GCGGTAGGCG TGCCTATGGG CGGTCTATAT AA      32

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (xi) SEQUENCE DESCRIPTION: SEQ ID NO:2:

GCGGTAGGCG TGCCTAATGG GAGGTCTATA TAA      33

(2) INFORMATION FOR SEQ ID NO:3:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (xi) SEQUENCE DESCRIPTION: SEQ ID NO:3:

```
CCCCATTGAC GCAAATGGGC GGTAGGCGTG TACGGTGGGA GGTCTATATA A        51
```

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:4:

```
GAAGAGGAAT TCGAATTCGA ATTCCTCTTC                                30
```

(2) INFORMATION FOR SEQ ID NO:5:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:5:

```
GCCRCCATGG                                                      10
```

(2) INFORMATION FOR SEQ ID NO:6:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:6:

```
CGCGTCAAAA AACCCCTCAS GACCCGTTTA GAGGCCCCAA GGGGTTATA          49
```

(2) INFORMATION FOR SEQ ID NO:7:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:7:

```
CGCGTATAAC CCCTTGGGGC CTCTAAACGG GTCTTGAGGG GTTTTTTGA          49
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

```
AAAAGGAAGA ATCCTGAGGC G                                         21
```

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

TGGACGAAGA ACATCAGGGG C                                                      21

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

TTGCTGAAGA ACTTGGCGGC G                                                      21

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:11:

AAGTCCATTC CTCTTCGTTA TTAATAGTAA TCAATT                                36

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:12:

AAGTCCATTC CTCTTCGCGG TAATACGGTT ATCCAC                                36

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:13:

AAGTCCATTC CTCTTCACCG AATGAGTGAG CTAACTTACA                          40

(2) INFORMATION FOR SEQ ID NO:14:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO:14:

AAGTCCATTC CTCTTCATAA TCGAATGGCG CAAAACCTTT CGCGGTATGG CATGATAGCG      60

CCCGAAAGAG                                                                           70

(2) INFORMATION FOR SEQ ID NO:15:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:15:

```
GATCCGGGGA ATTGTGAGCG GATAACAATT CCCC                          34
```

(2) INFORMATION FOR SEQ ID NO:16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:16:

```
GATCGGGGAA TTGTTATCCG CTCACAATTC CCCG                          34
```

(2) INFORMATION FOR SEQ ID NO:17:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:17:

```
AAGAATTTCA TAGCCGTCTC AGCAGCCAAC CGCTTTAAGA AAATCTCATC CTCCGGAGCA    60

CTTTGATAAC AGGTAAGTGT ACCCG                                          85
```

(2) INFORMATION FOR SEQ ID NO:18:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO:18:

```
GATCCGGGTA CACTTACCTG TTATCAAAGT GCTCCGGAGG ATGAGATTTT CTTAAAGCGG    60

TTGGCTGCTG AGACGGCTAT GAAAT                                          85
```

(2) INFORMATION FOR SEQ ID NO:19:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (xi) SEQUENCE DESCRIPTION: SEQ ID NO:19:

```
CATGCGAAGA GAATTCTCTT CACTTGTTCC GCGTGGTTTC AAACGTCGTT GGAA           54
```

(2) INFORMATION FOR SEQ ID NO:20:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (xi) SEQUENCE DESCRIPTION: SEQ ID NO:20:

TCTTTTTCCA ACGACGTTTG AAACCACGCG GAACAAGTGA AGAGAATTCT CTTCG        55

(2) INFORMATION FOR SEQ ID NO:21:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:21:

CTAGCTAATA CGACTCACTA TAGGGGAATT GTGAGCGGAT AACAATTCCC CTTTTGTTTA    60

ACTTTAAGAA GGAGAGGCCA C                                             81

(2) INFORMATION FOR SEQ ID NO:22:

(i) SEQUENCE CHARACTERISTICS:
        (A) LENGTH: 80 base pairs
        (B) TYPE: nucleic acid
        (C) STRANDEDNESS: single
        (D) TOPOLOGY: linear (xi) SEQUENCE DESCRIPTION: SEQ ID NO:22:

CATGGTGGCC TCTCCTTCTT AAAGTTAAAC AAAAGGGGAA TTGTTATCCG CTCACAATTC    60

CCCTATAGTG AGTCGTATTA                                               80

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:23:

AAGACCTAAG GATCCGGGTA CACTTACCTG TGA                                33

(2) INFORMATION FOR SEQ ID NO:24:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:24:

AAGACCTAAC GCTAGCTAAT ACGACTCACT ATAGG                              35

(2) INFORMATION FOR SEQ ID NO:25:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:25:

AATTCTAGTA AGC                                                      13

(2) INFORMATION FOR SEQ ID NO:26:

(i) SEQUENCE CHARACTERISTICS:
        (A) LENGTH: 13 base pairs
        (B) TYPE: nucleic acid
        (C) STRANDEDNESS: single (D) TOPOLOGY: linear (xi) SEQUENCE DESCRIPTION: SEQ ID NO:26:

AATTGCTTAC TAG                                                          13

(2) INFORMATION FOR SEQ ID NO:27:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:27:

GGCTGCTGAG ACGGCTATGA AATTCTTTTT CC                                     32

(2) INFORMATION FOR SEQ ID NO:28:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:28:

AAACTCTTCA TTCCAGACAT GATAGATACA TTG                                    33

(2) INFORMATION FOR SEQ ID NO:29:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:29:

AAACTCTTCA CGTTACCACA TTTGTAGAGG TTTTAC                                 36

(2) INFORMATION FOR SEQ ID NO:30:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:30:

AAACTCTTCA ACGCGTATAA CCCCTTGGG                                         29

(2) INFORMATION FOR SEQ ID NO:31:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:31:

AAACTCTTCA GAATCTAAAA TACACAAACA ATTAG                                  35

(2) INFORMATION FOR SEQ ID NO:32:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:32:

GGGCGGTAGG CGTGCCTAAT GGGAGGTCTA TATAAG                    36

(2) INFORMATION FOR SEQ ID NO:33:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:33:

CTTATATAGA CCTCCCATTA GGCACGCCTA CCGCCC                    36

(2) INFORMATION FOR SEQ ID NO:34:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:34:

GGGCGGTAGG CGTGCCTATG GCGGTCTAT ATAAG                      35

(2) INFORMATION FOR SEQ ID NO:35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:35:

CTTATATAGA CCGCCCATAG GCACGCCTAC CGCCC                     35

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:36:

AAGTTCTTCT CCTTTGCTAG CCAT                                 24

(2) INFORMATION FOR SEQ ID NO:37:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:37:

TGAAACCTCT TCAATGGCTA GCAAAGGAGA AGAACTTTTC AC             42

(2) INFORMATION FOR SEQ ID NO:38:

(i) SEQUENCE CHARACTERISTICS:
        (A) LENGTH: 38 base pairs
        (B) TYPE: nucleic acid
        (C) STRANDEDNESS: single
        (D) TOPOLOGY: linear -continued (xi) SEQUENCE DESCRIPTION: SEQ ID NO:38:

AAGTGATTGC TCTTCCAAGC TATTTGTATA GTTCATCC                                38

(2) INFORMATION FOR SEQ ID NO:39:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:39:

AGTTACTCTT CCAAGTTTGT ATAGTTCATC CATGCCATGT GTAATCC                      47

(2) INFORMATION FOR SEQ ID NO:40:

(i) SEQUENCE CHARACTERISTICS:
        (A) LENGTH: 5532 base pairs
        (B) TYPE: nucleic acid
        (C) STRANDEDNESS: double
        (D) TOPOLOGY: circular (xi) SEQUENCE DESCRIPTION: SEQ ID NO:40:

GCACTTTTCG GGGAAATGTG CGCGGAACCC CTATTTGTTT ATTTTTCTAA ATACATTCAA         60

ATATGTATCC GCTCATGAGA CAATAACCCT GATAAATGCT TCAATAATAT TGAAAAAGGA       120

AGAATCCTGA GGCGGAAAGA ACCAGCTGTG GAATGTGTGT CAGTTAGGGT GTGGAAAGTC       180

CCCAGGCTCC CCAGCAGGCA GAAGTATGCA AAGCATGCAT CTCAATTAGT CAGCAACCAG       240

GTGTGGAAAG TCCCCAGGCT CCCCAGCAGG CAGAAGTATG CAAAGCATGC ATCTCAATTA       300

GTCAGCAACC ATAGTCCCGC CCCTAACTCC GCCCATCCCG CCCCTAACTC CGCCCAGTTC       360

CGCCCATTCT CCGCCCCATG GCTGACTAAT TTTTTTTATT TATGCAGAGG CCGAGGCCGC       420

CTCGGCCTCT GAGCTATTCC AGAAGTAGTG AGGAGGCTTT TTTGGAGGCC TAGGCTTTTG       480

CAAAGATCGA TCAAGAGACA GGATGAGGAT CGTTTCGCAT GATTGAACAA GATGGATTGC       540

ACGCAGGTTC TCCGGCCGCT TGGGTGGAGA GGCTATTCGG CTATGACTGG GCACAACAGA       600

CAATCGGCTG CTCTGATGCC GCCGTGTTCC GGCTGTCAGC GCAGGGGCGC CCGGTTCTTT       660

TTGTCAAGAC CGACCTGTCC GGTGCCCTGA ATGAACTGCA AGACGAGGCA GCGCGGCTAT       720

CGTGGCTGGC CACGACGGGC GTTCCTTGCG CAGCTGTGCT CGACGTTGTC ACTGAAGCGG       780

GAAGGGACTG GCTGCTATTG GGCGAAGTGC CGGGGCAGGA TCTCCTGTCA TCTCACCTTG       840

CTCCTGCCGA GAAAGTATCC ATCATGGCTG ATGCAATGCG GCGGCTGCAT ACGCTTGATC       900

CGGCTACCTG CCCATTCGAC CACCAAGCGA AACATCGCAT CGAGCGAGCA CGTACTCGGA       960

TGGAAGCCGG TCTTGTCGAT CAGGATGATC TGGACGAAGA ACATCAGGGG CTCGCGCCAG      1020

CCGAACTGTT CGCCAGGCTC AAGGCGAGCA TGCCCGACGG CGAGGATCTC GTCGTGACCC      1080

ATGGCGATGC CTGCTTGCCG AATATCATGG TGGAAAATGG CCGCTTTTCT GGATTCATCG      1140

ACTGTGGCCG GCTGGGTGTG GCGGACCGCT ATCAGGACAT AGCGTTGGCT ACCCGTGATA      1200

TTGCTGAAGA ACTTGGCGGC GAATGGGCTG ACCGCTTCCT CGTGCTTTAC GGTATCGCCG      1260

CTCCCGATTC GCAGCGCATC GCCTTCTATC GCCTTCTTGA CGAGTTCTTC TGAGCGGGAC      1320

TCTGGGGTTC GAAATGACCG ACCAAGCGAC GCCCAACCTG CCATCACGAG ATTTCGATTC      1380

CACCGCCGCC TTCTATGAAA GGTTGGGCTT CGGAATCGTT TTCCGGGACG CCGGCTGGAT      1440

GATCCTCCAG CGCGGGGATC TCATGCTGGA GTTCTTCGCC CACCCTAGGG GGAGGCTAAC      1500

TGAAACACGG AAGGAGACAA TACCGGAAGG AACCCGCGCT ATGACGGCAA TAAAAAGACA      1560

```
GAATAAAACG CACGGTGTTG GGTCGTTTGT TCATAAACGC GGGGTTCGGT CCCAGGGCTG   1620

GCACTCTGTC GATACCCCAC CGAGACCCCA TTGGGGCCAA TACGCCCGCG TTTCTTCCTT   1680

TTCCCCACCC CACCCCCCAA GTTCGGGTGA AGGCCCAGGG CTCGCAGCCA ACGTCGGGGC   1740

GGCAGGCCCT GCCATAGCCT CAGGTTACTC ATATATACTT TAGATTGATT TAAAACTTCA   1800

TTTTTAATTT AAAAGGATCT AGGTGAAGAT CCTTTTTGAT AATCTCATGA CCAAAATCCC   1860

TTAACGTGAG TTTTCGTTCC ACTGAGCGTC AGACCCCGTA GAAAAGATCA AAGGATCTTC   1920

TTGAGATCCT TTTTTTCTGC GCGTAATCTG CTGCTTGCAA ACAAAAAAAC CACCGCTACC   1980

AGCGGTGGTT TGTTTGCCGG ATCAAGAGCT ACCAACTCTT TTTCCGAAGG TAACTGGCTT   2040

CAGCAGAGCG CAGATACCAA ATACTGTCCT TCTAGTGTAG CCGTAGTTAG GCCACCACTT   2100

CAAGAACTCT GTAGCACCGC CTACATACCT CGCTCTGCTA ATCCTGTTAC CAGTGGCTGC   2160

TGCCAGTGGC GATAAGTCGT GTCTTACCGG GTTGGACTCA AGACGATAGT TACCGGATAA   2220

GGCGCAGCGG TCGGGCTGAA CGGGGGGTTC GTGCACACAG CCCAGCTTGG AGCGAACGAC   2280

CTACACCGAA CTGAGATACC TACAGCGTGA GCTATGAGAA AGCGCCACGC TTCCCGAAGG   2340

GAGAAAGGCG GACAGGTATC CGGTAAGCGG CAGGGTCGGA ACAGGAGAGC GCACGAGGGA   2400

GCTTCCAGGG GGAAACGCCT GGTATCTTTA TAGTCCTGTC GGGTTTCGCC ACCTCTGACT   2460

TGAGCGTCGA TTTTTGTGAT GCTCGTCAGG GGGCGGAGC CTATGGAAAA ACGCCAGCAA   2520

CGCGGCCTTT TTACGGTTCC TGGCCTTTTG CTGGCCTTTT GCTCACATGT TCTTTCCTGC   2580

GTTATCCCCT GATTCTGTGG ATAACCGTAT TACCGTAATG AGTGAGCTAA CTTACATTAA   2640

TTGCGTTGCG CTCACTGCCC GCTTTCCAGT CGGGAAACCT GTCGTGCCAG CTGCATTAAT   2700

GAATCGGCCA ACGCGCGGGG AGAGGCGGTT TGCGTATTGG GCGCCAGGGT GGTTTTTCTT   2760

TTCACCAGTG AGACGGGCAA CAGCTGATTG CCCTTCACCG CCTGGCCCTG AGAGAGTTGC   2820

AGCAAGCGGT CCACGCTGGT TTGCCCCAGC AGGCGAAAAT CCTGTTTGAT GGTGGTTAAC   2880

GGCGGGATAT AACATGAGCT GTCTTCGGTA TCGTCGTATC CCACTACCGA GATATCCGCA   2940

CCAACGCGCA GCCCGGACTC GGTAATGGCG CGCATTGCGC CCAGCGCCAT CTGATCGTTG   3000

GCAACCAGCA TCGCAGTGGG AACGATGCCC TCATTCAGCA TTTGCATGGT TTGTTGAAAA   3060

CCGGACATGG CACTCCAGTC GCCTTCCCGT TCCGCTATCG GCTGAATTTG ATTGCGAGTG   3120

AGATATTTAT GCCAGCCAGC CAGACGCAGA CGCGCCGAGA CAGAACTTAA TGGGCCCGCT   3180

AACAGCGCGA TTTGCTGGTG ACCCAATGCG ACCAGATGCT CCACGCCCAG TCGCGTACCG   3240

TCTTCATGGG AGAAAATAAT ACTGTTGATG GGTGTCTGGT CAGAGACATC AAGAAATAAC   3300

GCCGGAACAT TAGTGCAGGC AGCTTCCACA GCAATGGCAT CCTGGTCATC CAGCGGATAG   3360

TTAATGATCA GCCCACTGAC GCGTTGCGCG AGAAGATTGT GCACCGCCGC TTTACAGGCT   3420

TCGACGCCGC TTCGTTCTAC CATCGACACC ACCACGCTGG CACCCAGTTG ATCGGCGCGA   3480

GATTTAATCG CCGCGACAAT TTGCGACGGC GCGTGCAGGG CCAGACTGGA GGTGGCAACG   3540

CCAATCAGCA ACGACTGTTT GCCCGCCAGT TGTTGTGCCA CGCGGTTGGG AATGTAATTC   3600

AGCTCCGCCA TCGCCGCTTC CACTTTTTCC CGCGTTTTCG CAGAAACGTG GCTGGCCTGG   3660

TTCACCACGC GGGAAACGGT CTGATAAGAG ACACCGGCAT ACTCTGCGAC ATCGTATAAC   3720

GTTACTGGTT TCACATTCAC CACCCTGAAT TGACTCTCTT CGGGCGCTA TCATGCCATA   3780

CCGCGAAAGG TTTTGCGCCA TTCGATTATT AATAGTAATC AATTACGGGG TCATTAGTTC   3840

ATAGCCCATA TATGGAGTTC CGCGTTACAT AACTTACGGT AAATGGCCCG CCTGGCTGAC   3900
```

```
-continued

CGCCCAACGA CCCCCGCCCA TTGACGTCAA TAATGACGTA TGTTCCCATA GTAACGCCAA    3960

TAGGGACTTT CCATTGACGT CAATGGGTGG AGTATTTACG GTAAACTGCC CACTTGGCAG    4020

TACATCAAGT GTATCATATG CCAAGTACGC CCCCTATTGA CGTCAATGAC GGTAAATGGC    4080

CCGCCTGGCA TTATGCCCAG TACATGACCT TATGGGACTT TCCTACTTGG CAGTACATCT    4140

ACGTATTAGT CATCGCTATT ACCATGGTGA TGCGGTTTTG GCAGTACATC AATGGGCGTG    4200

GATAGCGGTT TGACTCACGG GGATTTCCAA GTCTCCACCC CATTGACGTC AATGGGAGTT    4260

TGTTTTGGCA CCAAAATCAA CGGGACTTTC CAAAATGTCG TAACAACTCC GCCCCATTGA    4320

CGCAAATGGG CGGTAGGCGT GCCTAATGGG AGGTCTATAT AAGCAGAGCT GGTTTAGTGA    4380

ACCGTCAGAT CCGCTAGCTA ATACGACTCA CTATAGGGGA ATTGTGAGCG GATAACAATT    4440

CCCCTTTTGT TTAACTTTAA GAAGGAGAGG CCACCATGCG AAGAGAATTC TAGTAAGCAA    4500

TTGTTACTAG AATTGCTTAC TAGAATTCTC TTCACTTGTT CCGCGTGGTT TCAAACGTCG    4560

TTGGAAAAAG AATTTCATAG CCGTCTCAGC AGCCAACCGC TTTAAGAAAA TCTCATCCTC    4620

CGGAGCACTT TGATACCAGG TAAGTGTACC CGGATCCGGG GAATTGTGAG CGGATAACAA    4680

TTCCCCGATC CCCTTCCCAA CAGTTGCGCA GCCTGAATGG CGAATGGAGA TCCAATTTTT    4740

AAGTGTATAA TGTGTTAAAC TACTGATTCT AATTGTTTGT GTATTTTAGA TTCCAGACAT    4800

GATAAGATAC ATTGATGAGT TTGGACAAAC CACAACTAGA ATGCAGTGAA AAAAATGCTT    4860

TATTTGTGAA ATTTGTGATG CTATTGCTTT ATTTGTAACC ATTATAAGCT GCAATAAACA    4920

AGTTAACAAC AACAATTGCA TTCATTTTAT GTTTCAGGTT CAGGGGGAGA TGTGGGAGGT    4980

TTTTTAAAGC AAGTAAAACC TCTACAAATG TGGTAACGCG TATAACCCCT TGGGGCCTCT    5040

AAACGGGTCT TGAGGGGTTT TTTGACGCGT AAATTGTAAG CGTTAATATT TTGTTAAAAT    5100

TCGCGTTAAA TTTTTGTTAA ATCAGCTCAT TTTTTAACCA ATAGGCCGAA ATCGGCAAAA    5160

TCCCTTATAA ATCAAAAGAA TAGACCGAGA TAGGGTTGAG TGTTGTTCCA GTTTGGAACA    5220

AGAGTCCACT ATTAAAGAAC GTGGACTCCA ACGTCAAAGG GCGAAAAACC GTCTATCAGG    5280

GCGATGGCCC ACTACGTGAA CCATCACCCT AATCAAGTTT TTTGGGGTCG AGGTGCCGTA    5340

AAGCACTAAA TCGGAACCCT AAAGGGAGCC CCCGATTTAG AGCTTGACGG GGAAAGCCGG    5400

CGAACGTGGC GAGAAAGGAA GGGAAGAAAG CGAAAGGAGC GGGCGCTAGG GCGCTGGCAA    5460

GTGTAGCGGT CACGCTGCGC GTAACCACCA CACCCGCCGC GCTTAATGCG CCGCTACAGG    5520

GCGCGTCAGG TG                                                       5532
```

VECTOR FOR GENE EXPRESSION IN PROKARYOTIC AND EUKARYOTIC SYSTEMS

FIELD OF THE INVENTION

The invention concerns an expression vector that permits high level expression of genes (especially heterologous genes) and fragments thereof in both prokaryotic and eukaryotic systems. The invention also pertains to derivatives of such a vector that contain a prokaryotic or eukaryotic (especially mammalian) gene. The invention further pertains to prokaryotic or mammalian cells containing such an expression vector or derivative.

BACKGROUND OF THE INVENTION

The capacity to clone polynucleotides into autonomously replicating vectors has had a profound impact on medicine, biotechnology, and biological research. Typically, the fundamental differences between prokaryotic and eukaryotic cells has required the use of separate vectors whenever expression is desired in both classes of cells, or whenever a gene cloned in one class of cell is to be expressed in the other.

Because of fundamental differences between mammalian and prokaryotic cells, previously described vectors could not be used interchangeably to direct expression in both prokaryotic and mammalian cells. As a consequence, researchers seeking to express a gene of interest in both prokaryotic and mammalian cells needed to re-isolate and re-clone that gene into separate vectors, one suitable for prokaryotic expression, and one suitable for expression in mammalian cells. Each step involves isolation and characterization of clones containing the gene of interest, requiring a significant investment of time and biological reagents.

Thus, a large number of specialized prokaryotic vectors have been described (e.g., plasmids such as those capable of replication in *E. coli* such as, for example, pBR322, ColE1, pSC101, pACYC 184, πVX). Such plasmids are, for example, disclosed by Sambrook, J. et al. (In: *Molecular Cloning, A Laboratory Manual*, 2nd Ed., Cold Spring Harbor Press, Cold Spring Harbor, N.Y. (1989)). Sambrook, J. et al., herein incorporated by reference, provide a review of the characteristics of mammalian vectors (In: *Molecular Cloning, A Laboratory Manual*, 2nd Ed., Cold Spring Harbor Press, Cold Spring Harbor, N.Y. (1989).

For expression in mammalian cells, eukaryotic genes are typically cloned first into a bacterial vector and then subcloned into a vector suitable for eukaryotic expression. Thus, although many vectors have been described that are capable of replicating in both prokaryotic and eukaryotic cells, such vectors are designed to express a particular inserted polynucleotide in only one class of cell.

Such vectors are illustrated by U.S. Pat. No. 4,970,155 (Ikasinski, G. F.), which describes a prokaryotic plasmid that contains eukaryotic transcription and replication elements, such that an inserted polynucleotide can be expressed only in a eukaryotic cell. Similarly, U.S. Pat. No. 5,266,490 (Davis, S. et al.) describes an expression vector that contains an SV40 origin of replication, a eukaryotic transcription unit of the early immediate human cytomegalovirus (CMV) promoter region; and a generic polylinker and an SV40 splice/polyadenylation site. The vector also contains a pBR322 origin of replication and an antibiotic resistance gene under control of a prokaryotic promoter.

It is, however, desirable to have vectors that are capable of expressing an inserted gene in both prokaryotic and eukaryotic cells without any requirement to modify the vector or reclone the inserted gene. Recently, He, B. et al. (*Gene* 164: 75–79 (1995)) described expression vectors that direct the synthesis of proteins from a common set of signals in both prokaryotic and eukaryotic cells. To allow transcription from a common promoter the vectors rely upon a phage RNA polymerase. To direct initiation of translation to the same start codon the vectors utilize an internal ribosome entry site from encephalomyocarditis virus that has been modified to include a prokaryotic ribosome-binding site at an appropriate distance upstream from the desired start codon. Mole, S. E. et al. (*Nucl. Acids Res.* 15: 9090 (1987) describe pSEMCatR1, a prokaryotic-eukaryotic shuttle vector compatible with pUR and lambda gt11 expression systems. Kaehler, R. et al. (DD 206791) discuss a hybrid expression vector which contains prokaryotic and eukaryotic control units directly connected to the sequence being expressed. Alting-Mees, M. A. (*Strategies* 5:58–61 (1992) describes the Stratagene® vector pBK-CMV, which is intended to be suitable for gene expression in both prokaryotes and eukaryotes. However, genes cloned into pBK-CMV are expressed only inefficiently in eukaryotic cells.

In sum, for prior vectors, the isolation and characterization of clones containing the gene of interest requires a significant investment of time and biological reagents. The present invention eliminates the need to subclone from one vector system to another by combining the features of both vector systems into a single vector.

BRIEF DESCRIPTION OF THE FIGURES

FIG. 3 provides the sequences of CMV promoter mutants: RhCMV (SEQ ID NO:1: GCGGTAGGCGTGC-CTATGGGCGGTCTATATAA); AgMCMV (SEQ ID NO:2: GCGGTAGGCGTGCCTAATGGGAGG TCTATATAA); hCMV (SEQ ID NO:3: CCCCATTGACGCAAATGGGC GGTAGGCGTGTACGGTGGGAGGTCTATATAA). The Figure provides sequence comparisons of CMV IE gene promoters with a bacterial promoter and the consensus −10 and −35 promoter elements. Only the −10 and −35 hexamer sequences of the *E. coli* araBAD promoter are shown and aligned. The consensus −10 and −35 regions are shown in red and labeled accordingly. The underlined bases of the consensus regions indicate the nucleotides that are most highly conserved. The transcription start site of the hCMV promoter in prokaryotes that was mapped by primer extension assays is indicated with an arrow.

SUMMARY OF THE INVENTION

Figure 1:
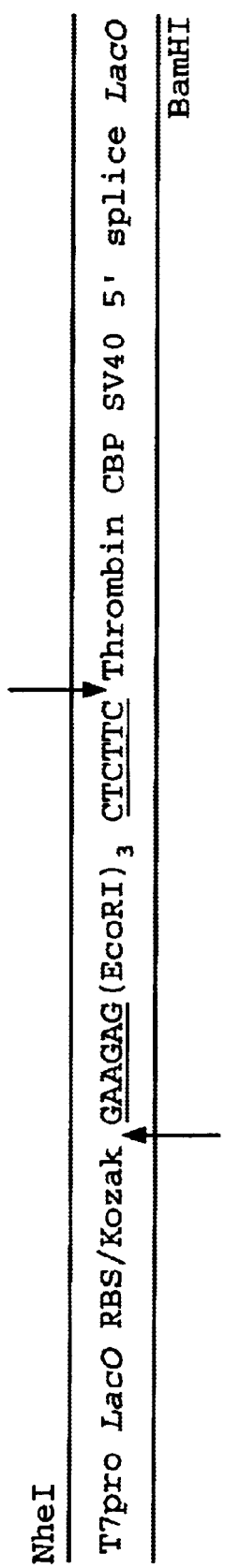
FIG. 1 provides a diagrammatic representation of the promoters and cloning site of a preferred dual vector. The Figure shows the design of the synthetic NheI/BamHI segment that replaced the lacZ sequences of the original pBK-CMV vector. The Eam1104I recognition sites are underlined and arrows indicate the location where cleavage occurs.

The invention concerns an expression vector that permits high level expression of genes and fragments thereof in both prokaryotic and eukaryotic systems. The invention also pertains to derivatives of such vector that contain one or more prokaryotic or eukaryotic (especially mammalian) genes or gene fragments. The invention further pertains to prokaryotic or mammalian cells containing such an expression vector or derivative.

In detail, the invention provides a dual expression vector, the vector comprising:

(A) a cloning site;
(B) transcription elements sufficient to permit transcription of a polynucleotide inserted into the cloning site in both a prokaryotic and a eukaryotic cell;
(C) translation elements sufficient to permit translation of an RNA transcript of the polynucleotide in both a prokaryotic and a eukaryotic cell; and
(D) replication elements sufficient to permit the replication of the vector in both a prokaryotic and a eukaryotic cell.

The invention particularly concerns such vectors (especially plasmid vectors), wherein the cloning site is a restriction site, and wherein the cloning site is flanked on each side by an Eam restriction site, the flanking Eam restriction sites being in inverted sequence orientation with respect to each other.

The invention further is directed to such vectors that possess an inducible prokaryotic promoter (e.g., a T7/LacO hybrid promoter, a trp promoter, a T7 promoter, a lac promoter, a bacteriophage lambda promoter). The invention further is directed to such vectors that possess a eukaryotic promoter (e.g., a metallothionein promoter, an SV40 promoter, a retroviral promoter, a cytomegalovirus promoter, a tissue-specific promoter, or a tumor-specific promoter).

The invention additionally concerns such vectors whose translation elements comprise a polynucleotide encoding a tag polypeptide, such that the inserted polynucleotide is expressed as a fusion protein having a carboxy-terminal tag (especially where the tag polypeptide permits the affinity purification of the expressed polynucleotide or wherein the fusion protein contains a cleavable linkage preceding the tag polypeptide, such that the tag polypeptide may be separated from an expression product of the inserted polynucleotide by a cleaving agent).

The invention particularly concerns the dual vector pdual.

The invention also concerns all of the above-described dual vectors wherein such vectors additionally comprise a polynucleotide (especially one encoding mammalian protein) inserted into the vector's cloning site.

The invention also concerns a process for expressing a protein encoding polynucleotide that comprises:
(A) inserting the polynucleotide into a vector that comprises:
  (1) a cloning site;
  (2) transcription elements sufficient to permit transcription of a polynucleotide inserted into the cloning site in both a prokaryotic and a eukaryotic cell;
  (3) translation elements sufficient to permit translation of an RNA transcript of the polynucleotide in both a prokaryotic and a eukaryotic cell; and
  (4) replication elements sufficient to permit the replication of the vector in both a prokaryotic and a eukaryotic cell;
(B) introducing the vector containing the inserted polynucleotide into a prokaryotic or a eukaryotic cell; and
(C) permitting the cell to express the polynucleotide.

The invention also provides a kit for expressing a protein encoded polynucleotide that comprises:
(A) a first container containing a vector that comprises:
  (1) a cloning site, comprising a restriction site, the cloning site being flanked on each side by an Eam restriction site, the flanking Eam restriction sites being in inverted sequence orientation with respect to each other;
  (2) transcription elements sufficient to permit transcription of a polynucleotide inserted into the site in both a prokaryotic and a eukaryotic cell;
  (3) translation elements sufficient to permit translation of an RNA transcript of the polynucleotide in both a prokaryotic and a eukaryotic cell; and
  (4) replication elements sufficient to permit the replication of the vector in both a prokaryotic and a eukaryotic cell; and
(B) a second container containing Eam restriction endonuclease for cleaving the Eam restriction sites of the vector of the first container.

DESCRIPTION OF THE PREFERRED EMBODIMENTS

The present invention is directed to improved expression vectors. As indicated above, prior efforts to produce vectors capable of mediating gene expression in both prokaryotic and eukaryotic cells have been encumbered by fundamental differences between eukaryotic and prokaryotic cells, and have failed to yield vectors having the ability to express a gene product at high levels in both eukaryotic and prokaryotic cells (Alting-Mees, M. A. (Strategies 5:58–61 (1992)). Indeed, genes cloned into the pBK-CMV described by Alting-Mees are expressed inefficiently in eukaryotic cells. Indeed, it has been found that removal of the lac sequences and modification of the pBK-CMV vector to contain a Kozak sequence between the NheI site and the multiple cloning site is required for high-level expression in eukaryotic cells. If the lac sequences are not removed, the level of expression in eukaryotes is very low, or undetectable. However, such alteration eliminates the capacity of the vector to express gene sequences in prokaryotic cells.

A second problem that has encumbered the development of vectors capable of mediating gene expression in both prokaryotic and eukaryotic cells is the difficulty of stably (i.e., non-transiently) expressing a gene product in both eukaryotic and prokaryotic cells. In this regard, Manoharan, H. T. et al. have recently described an expression vector that is stated to be capable of transiently expressing a mammalian protein (cyclin A) in both $E.\ coli$ and COS cells as a component of a large (242 amino acid long) modified GST fusion protein (Manoharan, H. T. et al., Gene 193:229–237 (1997)). The described vector however is not stated to have a prokaryotic origin of replication sufficient to permit its maintenance in prokaryotic cells, nor is it reported to be capable of mediating stable gene expression in either $E.\ coli$ or COS cells. The utility of the vector is limited by the size of the fusion tag, and by the fact many proteins do not express well as GST-fusions.

The present invention provides high level expression vectors that address and surmount these problems.

I. The High Level Expression Vectors of the Present Invention

As used herein, a "vector" is a nucleic acid molecule (either DNA or RNA) capable of autonomous replication upon introduction into a recipient cell. Plasmids, viruses and bacteriophages are preferred vectors. The process of "expression" is well known, and comprises the use of cellular enzymes and processes to produce a protein expression product from a polynucleotide. As used herein, a polynucleotide is a DNA or RNA molecule, typically of greater than about 50 bases, and more typically greater than 100 bases. The polynucleotides usable in the vectors and methods of the present invention may, however, be substantially larger (1–10 kb). Expression vectors are vectors that are capable of mediating the expression of a cloned polynucleotide. In a preferred embodiment, such polynucleotides will encode proteins or polypeptides, especially those having catalytic activity, hormonal activity or binding capacity (such as an antigen or hapten, a cellular receptor or a ligand for such a receptor, etc.).

The present invention concerns the design and use of vectors that are capable of permitting the high level transcription and translation of such polynucleotides in eukaryotic (especially mammalian, and most particularly, human, murine, simian, bovine, porcine or ovine cells) as well as in prokaryotic cells (especially *E. coli*, coliform enterics, Bacillus and Streptomyces). As used herein expression vectors capable of mediating such high level gene expression in both prokaryotic and eukaryotic cells (especially bacterial and mammalian cells) are termed "dual" expression vectors.

The vectors of the present invention comprise: a cloning site for receiving a polynucleotide; transcription elements sufficient to permit transcription of a polynucleotide inserted into said site in both a prokaryotic and a eukaryotic cell; translation elements sufficient to permit translation of an RNA transcript of said polynucleotide in both a prokaryotic and a eukaryotic cell and replication elements sufficient to permit the replication of said vector in both a prokaryotic and a eukaryotic cell. The vectors of the present invention are capable of mediating such expression transiently (i.e., without a requirement for the propagation of the vector within its host cell) or stably in prokaryotic and/or eukaryotic host cells. Most preferably, the vectors of the present invention will be capable of mediating such expression stably within the host cell.

The polynucleotides that may be inserted into the vectors of the present invention may be derived from any source, or may be non-naturally occurring (e.g., synthetic). In a preferred embodiment, such sequences will be "heterologous" polynucleotides (i.e., polynucleotides not naturally present in the particular prokaryotic or eukaryotic cell being employed as the host for the expression vector). Alternatively, however, the polynucleotides that may be used in the expression vectors of the present invention may be "homologous" polynucleotides (i.e., polynucleotides naturally present in the prokaryotic or eukaryotic cell being employed as the host for the expression vector. As used herein a mammalian protein is a protein naturally produced in a mammal. Similarly, a human protein is a protein naturally produced in a human.

The term "transcription elements" is intended to encompass the specialized sequences (such as operators, promoters) that are necessary to permit an RNA polymerase to initiate transcription of a polynucleotide. Transcription elements may also include transcription termination sequences, enhancer sequences, etc. that serve to facilitate or enhance the extent of transcription, or increase the stability of the transcript.

The vectors of the present invention will thus contain at least one promoter capable of being recognized by a prokaryotic RNA polymerase, and of thus permitting the transcription of a polynucleotide that is operably linked to that promoter. The vector may have multiple prokaryotic promoters if desired. The specific prokaryotic promoter(s) employed will depend upon the prokaryotic cell that is to be the host of the vector. Examples of suitable promoters include constitutive or inducible prokaryotic promoters, such as the λpL or λpR promoters, the T6 polymerase promoter, the T7 polymerase promoter, or other well-characterized promoters (e.g., lac, recA, gal, trp, ara, hut, etc.). Most preferably, the promoter used for expression in prokaryotic cells will be inducible. Where it is desired that the prokaryotic promoter be inducible, the dual vector may be adapted to additionally contain a gene encoding the repressor (or inducer) for that promoter. Thus, for example, the dual vectors of the present invention may regulate transcription from the Lac operator (LacO) by expressing the gene encoding the LacI repressor protein. Other examples include the use of the lexA gene to regulate expression of pRecA, the use of trpO to regulate ptrp, the λpL promoter may be employed in combination with the λCI gene to provide desired repression when transcription is not required. Alleles of such genes that increase the extent of repression (e.g., lacIq) or that modify the manner of induction (e.g., λCI857, rendering λpL thermo-inducible, or λCI+, rendering λpL chemo-inducible) may be employed.

The most preferred promoter is a hybrid T7/LacO promoter, which places the T7 promoter under repression by the lacI gene product. In the most preferred of such hybrid promoters, the T7 promoter sequence precedes the LacO sequence, such that transcription is directed from the T7 promoter. In such a promoter, the lacI gene product binds to the LacO sequences of the hybrid promoter, thereby preventing T7 RNA polymerase from reading through the sequence. Repression by the lacI gene product is eliminated by providing lactose or a galactose analog such as Isopropyl-β-D-thiogalactopyranoside (IPTG). Transcription from the T7 promoter thus occurs in the presence of IPTG since the lacI gene product is complexed by IPTG, and thus cannot bind to the LacO sequence.

Likewise, the vectors of the present invention will additionally comprise a promoter capable of permitting transcription in a eukaryotic host. Any of a variety of suitable eukaryotic promoters may be employed to mediate expression of dual vectors in eukaryotic cells. Where expression is desired in mammalian cells, the metallothionein promoter, an SV40 promoter, a retroviral promoter, the cytomegalovirus (CMV) promoter or tissue-specific or tumor-specific promoters such as the α-fetoprotein promoter, the amylase promoter (especially, the murine amylase promoter), the cathepsin E promoter, the M1 muscarinic receptor promoter, or the γ-glutamyl transferase promoter may be employed.

Suitable CMV promoter sequences can be obtained from the CMV-promoted β-galactosidase expression vector, CMVβ (MacGregor, G. R. et al., *Nucl. Acids Res.* 17:2365 (1989)). Suitable α-fetoprotein promoter sequences are present in the vectors PSVA F0.4 CAT$^A$ and PAF 5.1 (δ2-CAT) (Watanabe et al., *J. Biol. Chem.* 262:4812–4818 (1987)). The PSVA F0.4 CAT$^A$ vector contains 5 kb of flanking DNA with a deletion of approximately 2 kb between −1.0 and −3.0. The PAF 5.1 (δ2-CAT) vector encompasses approximately 400 base pairs of the α-fetoprotein 5' flanking sequence which lies between −3.7 kb and −3.3 kb, coupled to the SV40 promoter in the PSC1 CAT vector. Suitable amylase promoter, especially murine amylase promoter sequences are described by Wu et al. (*Molec. Cell. Biol.* 11:4423–4430 (1991)). Suitable cathepsin E promoter sequences are described by Azuma et al. (*J. Biol. Chem.* 267:1609–1614 (1992)). Suitable M1 muscarinic receptor promoter sequences are described by Fraser et al. (*Molec. Pharmacol.* 36:840–847 (1989)) and by Bonner (*Trends Neurosci.* 12:148–151 (1989)). Vectors containing suitable γ-glutamyl transferase promoter sequences are described by Rajagopalan, S. et al., *J. Biol. Chem.* 265:11721–11725 (1990).

The term "translation elements" is intended to encompass the specialized sequences (such as ribosome binding sites and initiation codons) that are necessary to permit translation of an RNA transcript into protein. Translation elements may also include consensus sequences leader sequences, splice signals, etc. that serve to facilitate or enhance the extent of translation, or increase the stability of the expressed product. The dual vectors of the present invention may possess ancillary transcription regions, such as introns, polyadenylation signals, Shine/Dalgarno translation signals and Kozak consensus sequences (Shine, J. et al., *Proc. Natl. Acad. Sci.* (U.S.A.) 71:1342–1346 (1974); Kozak, M., *Cell* 44:283–292 (1986)).

The term "replication elements" is intended to encompass the specialized sequences (such as origins of replication) that are necessary to permit replication of the vector in a host cell. In general, such vectors will contain at least one origin of replication sufficient to permit the autonomous stable replication of the vector in both a prokaryotic and a eukaryotic cell. Most preferably, such vectors will contain separate origins of replications that permit the vector to stably replicate in a prokaryotic and a eukaryotic cell.

To facilitate selection and maintenance of the vectors, they contain one or more selectable markers (such as polynucleotides that confer resistance to antibiotics, or a cellular capacity to grow on minimal medium, or in the presence of toxic metabolites).

II. Preferred Dual Expression Vectors of the Present Invention

The preferred pdual expression vector is derived from pBK-CMV which contains the CMV enhancer/promoter region necessary for gene expression in mammalian cells. The lactose promoter and lacZ sequences were removed from pBK-CMV and a unique synthetic segment (FIG. 1) was inserted into their place. The segment was designed to contain the phage T7 promoter followed by the lac operator (lacO) sequence which allows inducible gene expression in bacteria similar to the pET-11 vector series. To achieve translation of the mRNA produced in bacteria or mammalian cells, tandem Shine-Dalgarno/Kozak consensus sequence are present immediately following the hybrid T7/lacO promoter. The unique cloning region of the preferred dual expression vector is characterized by the presence of 2 Eam1104I recognition sequences directed in opposite orientations and separated by a spacer region encoding 3 EcoRI sites:

SEQ ID NO:4: GAAGAGGAATTCGAATTCGAATTC-CTCTTC

When the vector is digested with the Eam1104I restriction enzyme a 3-nucleotide 5' overhang is generated that is complementary to the ATG of a cDNA insert. In addition, for easy protein visualization using the Affinity™ CBP fusion detection kit (Stratagene) and/or for purification with a Calmodulin affinity resin (Stratagene), a Calmodulin Binding Peptide (CBP) is encoded as a C-terminal fusion tag. The CBP-affinity tag is preceded by a thrombin cleavage site which allows the removal of the fusion tag from the protein product of the polynucleotide of interest. Lastly, the 5' consensus splice site present in pBK-CMV and a second lacO sequence conclude the synthetic segment that replaced the original lac sequences present in the pBK-CMV expression vector.

Figure 2:
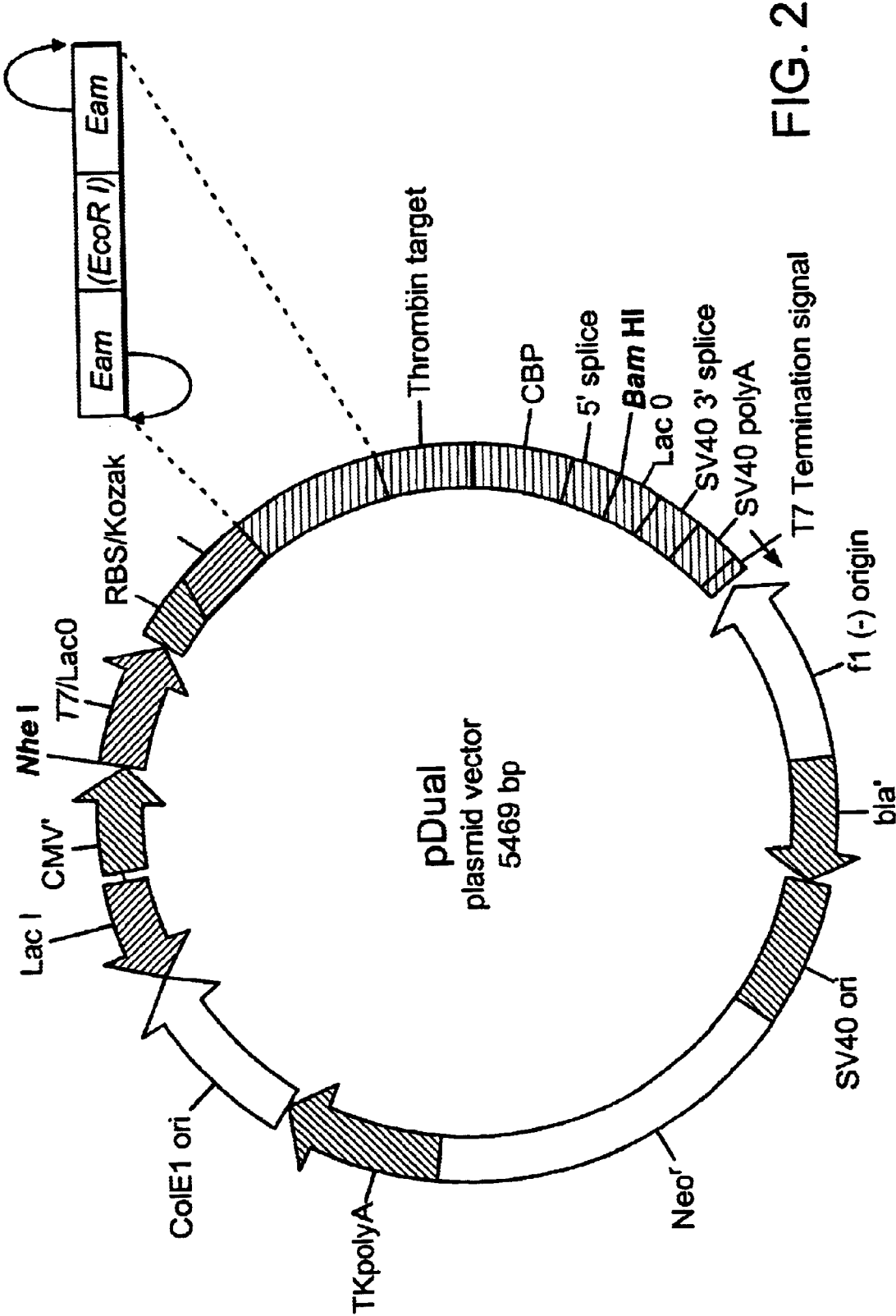
FIG. 2 provides a diagrammatic representation of the elements of the preferred dual expression vector, pdual.

The dual expression vectors of the present invention are further illustrated with reference to a particularly preferred embodiment (FIG. 2). Such a preferred dual vector contains ColE1 and f1(-) origins of replication to permit autonomous replication in a prokaryotic cell (*E. coli*). Additionally, the vector contains an SV40 origin of replication to permit replication in a eukaryotic cell. The vector additionally contains a dominant selectable marker (e.g., a neomycin phosphotransferase gene, sufficient to render recipient cells resistant to neomycin). To permit expression in both prokaryotic and eukaryotic cells, such dominant selectable marker is preferably under the dual control of both a promoter recognized in prokaryotes and a promoter recognized in eukaryotic cells.

The vector contains a constitutive CMV promoter and an inducible hybrid T7/LacO promoter. Efficient translation of mRNA encoding the polynucleotide of interest generated in either system is achieved by a tandemly arranged Shine-Dalgarno ribosome binding site (AAGGAG) for expression in prokaryotic cells, and a Kozak consensus sequence for expression in mammalian cells (see, Shine, J. et al., *Proc. Natl. Acad. Sci.* (U.S.A.) 71:1342–1346 (1974); Kozak, M., *Cell* 44:283–292 (1986)):

SEQ ID NO:5: GCC(A/G)CCATGG

To achieve efficient translation in both systems, the tandem translation initiation sequences are arranged so that each site is positioned at its optimum distance from the ATG (methionine) start codon.

Protein expression in bacteria is under the control of the strong T7 phage promoter. The phage promoter is arranged in tandem with a single lacO sequence (FIG. 1). The hybrid T7/LacO promoter serves to render the T7 polymerase promoter repressible by the Lac repressor (LacI gene product). Efficient repression of the promoter is achieved when the Lac repressor protein (LacI) binds to the lacO site and obstructs transcription by the T7 RNA polymerase. Lac repressor may be provided by the recipient cell, or, as in the case of the preferred dual vector, the vector may contain the LacI gene, and in a more preferred embodiment, the constitutively expressed allele of that gene, LacIq. As indicated, repression by LacI is eliminated by providing lactose or a galactose analog such as Isopropyl-β-D-thiogalactopyranoside (IPTG). The vector encodes the lacI gene which ensures high-level expression of lac repressor protein in bacterial cells.

In a preferred embodiment, the polynucleotide of interest is inserted into a restriction site, especially an Eam site, as described below.

In one embodiment, the insertion of the polynucleotide of interest permits the discreet synthesis of the encoded mRNA, and the translation of the mRNA into encoded protein free of additional amino acid or peptide residues. Alternatively, and more preferably, the insertion of the polynucleotide of interest will create an in-frame fusion with a second gene sequence, such that, upon expression, a fusion protein will be produced whose amino terminal portion corresponds to the protein encoded by the polynucleotide of interest and whose carboxyl terminal portion corresponds to the protein encoded by the second polynucleotide. In highly preferred embodiments, the second polynucleotide is selected such that it may be detected or recovered through the use of a specific affinity ligand. Examples of suitable second polynucleotides include those encoding antigens, haptens, cell receptors or ligands, etc. A polynucleotide that encodes a calmodulin binding peptide (CBP) is particularly preferred for this purpose. In a highly preferred sub-embodiment, the expressed fusion will be designed to contain a cleavable linkage, such that the expressed product of the polynucleotide of interest can be separated from the remaining portion of the fusion protein by cleaving the fusion product. Depending upon the precise amino acid sequence of such proteins, any of a variety of proteases or endopeptidases may be employed. For example, the use of a CBP-affinity tag located downstream of the cloning site allows simple detection and purification of the protein encoded by a gene of interest. The CBP-affinity tag can be removed by engineering the vector to contain a thrombin cleavage site immediately preceding the tag. The thrombin cleavage sequence is a particularly preferred cleavable linkage.

Most preferably, the dual vector will also contain a consensus 5' splice site, as well as an SV40 3' splice site, or should contain another intron. To facilitate expression in eukaryotic cells, the vectors may also contain an SV40 polyA site. The SV40 late polyA signal is a preferred signal for this purpose, since it increases the efficiency of polyadenylation, which in turn augments the stability of mRNA in eukaryotic cells (Carswell, S. et al., *Molec. Cell. Biol.* 9:4248–4258 (1989)). In addition, to abrogate the possibility of uncontrolled or "runaway" transcription in bacterial cells, a T7 transcription termination site is preferably provided downstream of the SV40 poly(A) signal (FIG. 2). In a preferred dual vector, a gene encoding a polyadenylation signal (such as the TKpolyA signal) is also present. The dual vectors of the present invention may also have additional elements or regions (such as restriction recognition sites, amino terminal expression tags, etc.), if desired.

As indicated above, the polynucleotide of interest is preferably to be inserted into a restriction site of a dual vector. By engineering the dual vectors of the present invention to lack Eam restriction sites, the polynucleotide of interest can be inserted into the vector in conjunction with Stratagene's Seamless cloning technique (Padgett, K. A. et al., *Gene* 168:31–35 (1996); Padgett, K. A. et al., *Strategies* 9:14–16 (1996), both herein incorporated by reference). In this regard, the most preferred dual expression vectors have been designed to lack Eam1104I sites. In the Seamless cloning method, PCR amplification of the polynucleotide of interest is conducted using primers that contain the Eam1104I (Eam) restriction site and a minimal flanking sequence. As a consequence, the amplification process installs Eam sites onto both ends of the polynucleotide of interest. Such sites may be cleaved by the type IIS Eam restriction enzyme. After digesting the PCR product with Eam, the fragment can be inserted via a 3 nucleotide 5' overhang encoding the gene's own ATG. The use of the type IIS Eam restriction enzyme eliminates primer-related residual nucleotides that are generally present when regular restriction enzyme recognition sites are encoded by the PCR primer sequences.

III. Uses of the Preferred Expression Vectors of the Present Invention

The dual expression vectors of the present invention may be used to clone and/or express any gene sequence, whether naturally occurring or synthetic, in both a prokaryotic and a eukaryotic cell. In particular, such vectors facilitate the isolation, manipulation and study of eukaryotic genes, gene fragments and cDNA transcripts.

The preferred dual vectors of the invention permit the expression of polynucleotides as fusion proteins. Because PCR cloning is extremely versatile, the researcher has the option to fuse the gene of interest to the small calmodulin binding peptide (CBP) affinity tag by simply eliminating the gene's natural termination codon. The 4 kD CBP fusion tag, expressed on the carboxy-terminal (C-terminal) of the protein, can then be used for easy detection and purification of the fusion protein using Stratagene's Affinity detection and purification system.

One aspect of the present invention concerns kits for using the dual vectors of the invention. In one such kit, the vector is provided in supercoiled form with reagents and instructions for its use. Alternatively, the vectors of such kits may be provided as linear molecules, pre-digested with Eam1104I.

Having now generally described the invention, the same may be more readily understood through the following reference to the following examples, which are provided by way of illustration and are not intended to be limiting of the present invention unless specified.

EXAMPLE I

Construction of the pDual Prokaryotic/Mammalian Expression Vector

The pdual prokaryotic/mammalian expression vector was constructed in multiple steps. The first step of the construction was the insertion of the T7 termination signal into plasmid pBK-CMV. To accomplish this, 2 μg of pBK-CMV was digested with 10 units of Mlu 1 in a 20 μl reaction containing 2× universal buffer and 1 unit calf intestinal alkaline phosphatase (CIAP, Stratagene). The digest was incubated for 1 hr at 37° C. and divided into two aliquots. One aliquot of the digest was fractionated by gel electrophoresis on a 1% TAE-agarose gel supplemented with ethidium bromide at a concentration of 0.5 μg per ml. The fractionated DNA was excised and purified with Geneclean (Bio101). The other aliquot of the digest was purified using Strataclean (Stratagene).

200 ng of each synthetic oligo (Table 1, 1F/1R) comprising the T7 termination signal were mixed and annealed by incubating for 10 min. at 75° C. and then allowing the mixture to cool to room temperature over a period of 1 h. Digested vector (0.07 pmol) was ligated with 0.67 pmol of the annealed oligonucleotides in a total reaction volume of 20 μl containing 400 units of T4 DNA ligase (New England Biolabs), 0.1 volumes of 10× ligation buffer supplemented with 1 mM ATP (New England Biolabs). The ligation reaction was incubated 2 h at room temperature. As a consequence of this step, a T7 transcription termination site was inserted into the MluI site immediately downstream of the SV40 poly(A) signal.

TABLE 1

| SEQ ID NO: | Oligo No. | Oligonucleotide Sequence |
|---|---|---|
| 6 | 1F | CGCGTCAAAAAACCCCTCASGACCCGTTTAGAGGCCCCAAGGGGTTATA |
| 7 | 1A | CGCGTATAACCCCTTGGGGCCTCTAAACGGGTCTTGAGGGGTTTTTTGA |
| 8 | 2 | AAAAGGAAGAATCCTGAGGCG |
| 9 | 3 | TGGACGAAGAACATCAGGGGC |
| 10 | 4 | TTGCTGAAGAACTTGGCGGCG |
| 11 | 5F | AAGTCCATTCCTCTTCGTTATTAATAGTAATCAATT |
| 12 | 5R | AAGTCCATTCCTCTTCGCGGTAATACGGTTATCCAC |
| 13 | 6F | AAGTCCATTCCTCTTCACCGAATGAGTGAGCTAACTTACA |
| 14 | 6R | AAGTCCATTCCTCTTCATAATCGAATGGCGCAAAACCTTTCGCGGTATGGCATGATAGCGCCCGAAAGAG |
| 15 | 7F | GATCCGGGGAATTGTGAGCGGATAACAATTCCCC |
| 16 | 7R | GATCGGGGAATTGTTATCCGCTCACAATTCCCCG |
| 17 | 8F | AAGAATTTCATAGCCGTCTCAGCAGCCAACCGCTTTAAGAAAATCTCATCCTCCGGAGCACTTTGATAACAGGTAAGTGTACCCG |
| 18 | 8R | GATCCGGGTACACTTACCTGTTATCAAAGTGCTCCGGAGGATGAGATTTTCTTAAAGCGGTTGGCTGCTGAGACGGCTATGAAAT |
| 19 | 9E | CATGCGAAGAGAATTCTCTTCACTTGTTCCGCGTGGTTTCAAACGTCGTTGGAA |
| 20 | 9R | TCTTTTTCCAACGACGTTTGAAACCACGCGGAACAAGTGAAGAGAATTCTCTTCG |
| 21 | 10F | CTAGCTAATACGACTCACTATAGGGGAATTGTGAGCGGATAACAATTCCCCTTTTGTTTAACTTTAAGAAGGAGAGGCCAC |
| 22 | 10R | CATGGTGGCCTCTCCTTCTTAAGTTAAACAAAAGGGGAATTGTTATCCGCTCACAATTCCCCTATAGTGAGTCGTATTA |
| 23 | 11F | AAGACCTAAGGATCCGGGTACACTTACCTGTGA |
| 24 | 11R | AAGACCTAACGCTAGCTAATACGACTCACTATAGG |
| 25 | 12F | AATTCTAGTAAGC |
| 26 | 12R | AATTGCTTACTAG |
| 27 | 13 | GGCTGCTGAGACGGCTATGAAATTCTTTTTCC |
| 28 | 14F | AAACTCTTCATTCCAGACATGATAGATACATTG |
| 29 | 14R | AAACTCTTCACGTTACCACATTTGTAGAGGTTTTAC |
| 30 | 15F | AAACTCTTCAACGCGTATAACCCCTTGGG |
| 31 | 15R | AAACTCTTCAGAATCTAAAATACACAAACAATTAG |
| 32 | 16F | GGGCGGTAGGCGTGCCTAATGGGAGGTCTATATAAG |
| 33 | 16R | CTTATATAGACCTCCCATTAGGCACGCCTACCGCCC |

TABLE 1-continued

| SEQ ID NO: | Oligo No. | Oligonucleotide Sequence |
|---|---|---|
| 34 | 17F | GCGCGGTAGGCGTGCCTATGGGCGGTCTATATAAG |
| 35 | 17R | CTTATATAGACCGCCCATAGGCACGCCTACCGCCC |
| 36 | 18 | AAGTTCTTCTCCTTTGCTAGCCAT |
| 37 | 19F | TGAAACCTCTTCAATGGCTAGCAAAGGAGAAGAACTTTTCAC |
| 38 | 19R | AAGTGATTGCTCTTCCAAGCTATTTGTATAGTTCATCC |
| 39 | 20 | AGTTACTCTTCCAAGTTTGTATAGTTCATCCATGCCATGTGTAATCC |

100 μl XL-2 Blue ultra competent bacterial cells (Stratagene) were transformed with 2 μl of the ligation reaction following the manufacturer's protocol, except that the β-mercaptoethanol was omitted. The heat-pulsed cells were allowed to recover in 900 μl NZY broth for h at 37° C. with shaking. 100 μl of the transformed cells were plated on NZY medium supplemented with 75 μg/ml of kanamycin (NZY/kan). Several clones were characterized. One clone (No. 2656-68.9) was chosen for the next step of construction (Table 2).

Clone No. 2656-68.9 was then treated to abolish its four Eam1104I restriction sites. The Eam1104I site at position 914 in clone No. 2656-68.9 was eliminated by digesting with PvuI, removing the 3' overhang with cloned Pfu DNA polymerase (Stratagene) in the presence of dGTP then digesting with BamHI and refilling the 5' overhang with the Klenow fragment of DNA polymerase I (Stratagene) in the presence of all four of dNTPs.

TABLE 2

| | Constructs | Comments/Properties |
|---|---|---|
| 1. | pBK-CMV | Parental Expression Vector. Neomycin selection. Poor expression in eukaryotes. Inducible expression in prokaryotes. |
| 2. | Clone #2656-68.9 | Clone with T7 termination signal inserted at MluI site of pBK-CMV. |
| 3. | Clone #2656-85.7 | Clone with Eam1104I site at position 914 of 2656-68.9 removed. |
| 4. | Clone #2686-10.12 | Clone with last 3 Eam1104I sites of 2656-85.7 abolished. |
| 5. | Clone #2686-34.40 | LacI gene inserted into 2686-10.12. |
| 6. | Clone #2721-45.1 | BamHI/NheI fragment inserted into BamHI/NheI digested 2686-34.40. |
| 7. | Clone #2721-54.1 | LacO sequence inserted into BamHI site of 2721-45.1 |
| 8. | Clone #2757-73.18 | revised BamHI/NheI fragment inserted into clone 2721-54.1 containing a 2 bp deletion of the CBP-ffinity tag coding region |
| 9. | Clone #2757-92.4 | Synthetic EcoRI stuffer fragment inserted into EcoRI site of 2757-73.18 |
| 10. | Clone #2800-9.12 (first pdual vector) | 2 bp deletion of CBP-affinity tag coding region repaired. |
| 11. | Clone #2995-57.2 (second pdual vector) | SV40 early polyA signal replaced with SV40 late polyA signal. Neomycin selection. Cloning site compatible with Seamless cloning techniques. Improved mRNA stability in eukaryotes. Constituitive high-level expression in both eukaryotes and prokaryotes. Expressed protein purifiable by cleavable CBP-affinity tag. |
| 12. | Clone #2995-71 Rh-3 | CMV promoter of 2995-57.2 altered to remove cryptic bacterial initiation site. Neomycin selection. Cloning site compatible with Seamless cloning techniques. Constituitive high-level expression in eukaryotes. Inducible high-level expression in prokaryotes. Expressed protein purifiable by thrombin-cleavable CBP-affinity tag. |
| 13. | Clone #2995-71 AgM-3 (final pdual vector) | CMV promoter of 2995-57.2 altered to remove cryptic bacterial initiation site. Neomycin selection. Cloning site compatible with Seamless cloning techniques. Constituitive high-level expression in eukaryotes. Inducible high-level expression in prokaryotes. Expressed protein purifiable by thrombin-cleavable CBP-affinity tag. |
| 14. | Clone #KP 2833-7.11 | GFP cloned into Clone #2800-9.12. Constitutive expression of GFP in prokaryotes. Constituitive high-level expression of GFP in eukaryotes. Expressed GFP purifiable by thrombin-cleavable, CBP-affinity tag expressed. |
| 15. | Clone #KP 2800-47.3 | GFP cloned into Clone #2800-9.12. Constitutive expression of GFP in prokaryotes. Constituitive high-level expression of GFP in eukaryotes. Does not express CBP tag |
| 16. | Clone #KP 2995-87.6 | GFP cloned into final pdual vector 2995-71AgM-3 Constituitive high-level expression of GFP in eukaryotes. Inducible high-level expression of GFP in prokaryotes. Expressed GFP purifiable by thrombin-cleavable, CBP-affinity tag expressed. |
| 17. | Clone #KP 2995-87.27 | GFP cloned into vector 2995-71Rh-3 Constituitive high-level expression of GFP in eukaryotes. Inducible high-level expression of GFP in prokaryotes. CBP-affinity tag expressed. |

The vector, blunted in this manner, was then religated to re-create a unique BamHI site. Several clones were characterized and clone No. 2656-85.7 was chosen for site-directed mutagenesis to eliminate the other 3 Eam1104I sites (Table 2). The Chamelion double stranded DNA mutagenesis kit (Stratagene) was used to introduce the site-specific changes that eliminated the Eam1104I restriction sites following the manual supplied with the kit. Three mutagenic primers (Table 1, Oligo Nos. 2, 3 and 4) were designed to change a single nucleotide within the Eam1101I recognition sequence, but to conserve the amino acid sequence. Several of the resulting clones were characterized and Clone No. 2686-10.12 was chosen for subsequent construction (Table 2).In the next step of the construction of pdual, the lacI gene, with its own promoter, was introduced into Clone No. 2686-10.12. The gene was inserted into the pdual expression vector in opposite orientation to the vector's CMV-promoter, to ensure that read-through was kept to a minimum. This was accomplished by amplifying clone No. 2686-10.12 with Oligo Nos. 5F/5R (Table 1) via PCR (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; Saiki, R. et al., U.S. Pat. No. 4,683,194 and Higuchi, R. "PCR Technology," Ehrlich, H. (ed.), Stockton Press, NY, 1989, pp 61–68), which references are incorporated herein by reference). Thus, 1.5 μl 2686-10.12 miniprep DNA template was combined with 18.3 pmol of each primer, 200 µM of each dNTP, 5 units Taq DNA polymerase (Stratagene) and 5 units of Taq Extender PCR additive (Stratagene) in 1× cloned Pfu buffer. The total volume was 100 µl and the reaction was amplified for 1 cycle at 94° C. for 3 min/58° C. for 2 min/72° C. for 5 min. and 30 additional cycles at 40 sec/40 sec/4.5 min, respectively.

The lacI gene was amplified via PCR using Oligo Nos. 6F/6R (Table 1). This was done by combining 1 µl of pLiz miniprep DNA template with 16.5 pmol of the forward primer, 9.4 pmol of the reverse primer, 200 mM of each dNTP, 2.5 units of Taq DNA polymerase and 5 units of Taq Extender PCR additive in 1× cloned Pfu buffer. The total volume was 100 µl and the reaction was amplified for 1 cycle at 94° C. for 3 min/54° C. for 1 min/72° C. for 2 min. and 30 additional cycles at 94° C. for 45 sec/54° C. for 35 sec/72° C. 1.5 min.

Both PCR reactions were phenol:chloroform extracted and the products were precipitated. The products were digested separately at 37° C. in a 20 µl reaction volume containing 4 units of EarI (Eam1104I isoschizomer, New England Biolabs) in 1× universal buffer. Ligation of the digested PCR products was performed in a 20 µl reaction volume as described previously, except that the ligation reaction was incubated overnight at 14° C. 100 µl XL-2Blue ultra competent cells (Stratagene) were transformed with 4 µl of the ligation reaction and grown on NZY/kan medium. Clone No. 2686-34.40 was chosen for the next step in the vector construction (Table 2).

The inserted gene was tested for production of a functional Lac repressor protein, by transforming the vector into SCS1 *E. coli* cells. This bacterial strain contains a single copy of the wild type lac operon and although the lac repressor protein is expressed from the lac operon in the chromosome of this bacterium, not enough protein is made to control β-galactosidase production. Consequently, constitutive low level expression of the lacZ gene results in blue colonies when the bacteria are grown in the presence of X-Gal. Introduction of a plasmid containing a functional lacI gene results in the complete repression of β-galactosidase production in SCS1 cells and the growth of white bacterial colonies. This experiment indicated that the lacI gene, located on the pdual vector, was indeed functional since only white colonies were observed when SCS1 cells harboring this construct were plated on X-Gal containing medium. SCS1 cells transformed with the original pBK-CMV plasmid or the parental clone, neither of which contained the lacI gene, yielded only blue colonies.

The next step of the construction was the insertion of a synthetic BamHI/NheI fragment into Clone No. 2686-34.40. This was accomplished using 3 sets of complementary oligonucleotides (Table 1; Oligo Nos. 8F/8R, 9F/9R, 10F/10R). These oligonucleotides were annealed to one another at a concentration of approximately 200 pmol using the method described above. The 3 sets of annealed oligonucleotides where then ligated together for 1 hr at room temperature at a concentration of approximately 50 pmol per pair using the method described above. The ligation product (2 µl) was PCR amplified (for 1 cycle at 95° C. for 3 min/50° C. for 2 min/72° C. for 1 min. followed by 25 cycles of 30 sec per step) with 10 pmol of each primer (Table 1; Oligo No. 11F/11R), 200 µM of each dNTP, 2.5 units of Taq DNA polymerase in 1× Taq buffer. A portion of the product was polished with Pfu DNA polymerase and cloned into PCR-script (Stratagene,) according to the manual supplied with the kit.

Several PCRscript clones were pooled, the insert was cut out as a BamHI/NheI fragment and was subcloned into the similarly digested clone No. 2686-34.40. Several clones were sequenced and Clone No. 2721-45.1 was chosen for the next step of inserting a synthetic lacO sequence.

All sequencing reactions were performed with $^{33}$Pα-dATP using either the Sequenase 2.0 kit (USB) or the Cyclist Exo$^-$ Pfu DNA sequencing kit (Stratagene) according to the instructions supplied with each kit. The sequencing reactions were fractionated on pre-poured 6% Cast-Away sequencing gels (Stratagene) and visualized by autoradiography on BioMax film (Kodak).

To insert a synthetic lacO sequence into Clone No. 2721-45.1, complimentary oligonucleotides (Table 1; Oligo Nos. 7F/7R) comprising the lacO sequence were annealed to each other using the annealing procedure described above. 7.5 fmol BamHI digested vector and 2.0 fmol of annealed oligonucleotides were ligated together for 2 h at room temperature and transformed into XL-1Blue supercompetent cells (Stratagene) as described previously. Clone No. 2721-54.1 was chosen for further vector construction (Table 2).

Next, the synthetic BamHI/NheI fragment of Clone No. 2721-54.1 was replaced with a modified synthetic BamHI/NheI fragment that contains 2 functional stop codons and a mutation to abolish translation from an alternative start site. To do this, the primers containing the modified sequences were annealed and ligated as described above. The PCR amplification of the synthetic fragment was repeated as described previously (1 cycle at 94° C. for 2 min/50° C. for 1 min/72° C. for 1 min. followed by 15 cycles of 45 sec per step), except that the PCR additive Taq Extender was added and cloned Pfu buffer was used instead of Taq buffer. The resultant PCR product was then cloned into pCR-Script. Several pCR-Script clones were pooled, the inserts were subcloned into Clone No. 2721-54.1 as BamHI/NheI fragments.

Of 24 clones that were sequenced, all contained mutations at different sites and to varying degrees. Clone No. 2757-73.18 was chosen because it contained that least detrimental mutation: a deletion of 2 base pairs in the CBP-affinity tag (Table 2).

A synthetic EcoRI stuffer fragment was next inserted into the EcoRI site of Clone No. 2757-73.18. This was accomplished using complementary oligonucleotides (Table 1, Oligo Nos. 12F/12R), which were annealed as described above, using 1 nmol of each oligo. 0.1 pmol of annealed EcoRI stuffer and 0.01 pmol of EcoRI-digested, dephosphorylated vector were ligated together and transformed as previously described. Several clones were sequenced and Clone No. 2757-92.4 was chosen for the next step (Table 2).

The Chamelion kit (Stratagene) was used to introduce the missing nucleotides in the CBP-tag in a site-specific manner. The mutagenic primer (Table 1, Oligo No. 13) was designed according to the recommendations in the manual containing 32 nucleotides, with approximately 13–15 bases flanking the desired sequence changes. The selection primer used in this particular reaction was the CspI→SanDI primer (Stratagene), which is specific for the neomycin gene located in pBK-CMV. All steps were performed according to the manual provided with the kit. Several clones were sequenced and Clone No. 2800-9.12 was chosen for further manipulation.

Next, the polyadenylation (polyA) signal in clone 2800-9.12 was changed. The change of the polyA sites was done via the Seamless™ cloning kit (Stratagene) using primers that contained Eam1104I restriction sites. The late polyA signal was amplified with primer set Oligo Nos. 14F/14R (Table 1) from the mammalian expression vector pCI-neo (Promega). The vector backbone of Clone No. 2800-9.12 was amplified with primer set Oligo Nos. 15F/15R (Table 1) in the presence of 5-methyl dCTP according to the instructions supplied with the Seamless™ cloning kit, except that 5.5 ng of Pfu accessory protein was added to the reaction and the extension time was reduced from 12 min. to 6 min. Seven of the 12 colonies screened by restriction digest contained the correct late polyA signal. Clone No. 2995-57.2 was chosen as the parental vector (Table 2).

Next, the CMV promoter of Clone No. 2995-57.2 was mutagenized in several places within a 15 nucleotide span immediately preceding the TATA box of the CMV promoter, using the QuickChange mutagenesis kit (Stratagene). The mutagenic primers Oligo Nos. 16F/16R (Table 1) were designed to contain 5 consecutive nucleotide changes and mutagenic primer set Oligo Nos. 17F/17R featured 6 changes, including a deletion. The mutations were engineered to lie in the middle portion of the oligonucleotides, with 12–17 bases of correct flanking sequence. The primers were PAGE purified as suggested in the kit's instruction manual. The reactions were carried out according to the instructions supplied in the manual, except that an additional 5.5 ng of Pfu accessory protein was added to the reaction and the extension time was reduced to 1 min. per kb. Eight clones of each mutagenic primer set were sequenced.

Two clones mutagenized with primer set Oligo Nos. 17F/17R contained the desired mutations. Seven clones mutagenized with primer set Oligo Nos. 16F/16R contained the desired mutations. Clone No. 2995-71AgM-3 was chosen as the final pdual expression vector. XL1-Blue supercompetent bacteria (Stratagene) were transformed with the ligation product and 18 colonies were screened by PCR for the presence of the reporter gene. One hundred percent of the screened colonies contained the desired insert and one of the clones, designated GFP Clone No. 2995-87.6, was chosen for further study (Table 2).

Plasmid DNA was obtained as follows. A 500 ml bacterial culture harboring the desired construct was grown overnight and then centrifuged for 5–10 min. at 5000 rpm at 4° C. The pellet was resuspended in 10 ml of 50 mM Tris, pH 7.5. 2 ml of 10 mg/ml lysozyme were added and the mixture was incubated on ice for 5 min. 0.75 ml of 0.5 M EDTA was then added and the solution was kept on ice for another 5 min. 0.5 ml of 2% TritonX-100 detergent was added drop-wise while the cells were vortexed and the sample was incubated on ice for an additional 20 min. The sample was then cleared of genomic DNA and protein by centrifugation at 4° C. for 30–45 min. at 12,000 rpm in a Sorval high speed centrifuge equipped with an SS34 rotor. The supernatant was transferred to a fresh 50 ml centrifuge tube and extracted with 12 ml phenol:chloroform:isoamyl alcohol. The aqueous phase was separated from the organic phase and transferred to a fresh centrifuge tube. The crude plasmid was precipitated from the aqueous phase by addition of 10 ml isopropyl alcohol and a 20 min. centrifugation step as above. The resulting pellet was briefly dried and resuspended in 2 ml TE (10:1). 8 µl of RNAce-It™ ribonuclease cocktail (Stratagene) was added to the resuspended DNA and the solution was incubated at 37° C. for 1 h. Subsequently 80 µl of 10 mg/ml Proteinase K (Stratagene) was added and the sample was incubated for an additional hour at 37° C. The plasmid DNA was precipitated by adding 0.5 ml of 5M NaCl and 0.75 ml of a 30% PEG-8000 solution and subsequent incubation of on ice for a period of 2 h to overnight. The sample was then centrifuged for 20 min. at 12,000 rpm and the supernatant was discarded. The pellet was dried briefly, resuspended in 2 ml TE (10:1) and extracted with 2 ml phenol:chloroform:isoamyl alcohol as described above. The plasmid DNA was then precipitated from the aqueous layer with 0.1 volume of 10×STE and 2.5 volumes of ice-cold 100% ethanol and gentle inversion of the solution. The DNA precipitate was centrifuged immediately and the pellet was dried in vacuo and resuspended in 1–2 ml TE. Optical density measurements were taken at 260 nm and 280 nm to determine the nucleic acid and protein concentration of the sample. In general, a 260/280 ratio of 1.8 or better is achieved with this method and the DNA concentration is generally in the range of 1–3 mg.

EXAMPLE IIA

Insertion of the GFP Reporter Gene into the First Dual Vector

It was of course essential to validate the vector's capability to express heterologous genes in both prokaryotic and eukaryotic cells.

To assess the dual function of the vector, expression was investigated using vector constructs that expressed either a native reporter or a reporter-CBP fusion protein. The green fluorescent protein (GFP) (Chalfie, M. et al. *Science* 263:802–805 (1994), herein incorporated by reference) was chosen as the reporter molecule because its production can be easily visualized in bacterial colonies using a long-wave UV light source. Its presence in transfected mammalian cells can be determined using standard fluorescence microscopy.

A polynucleotide encoding GFP was cloned into dual vector 2800-9.12, such that the GFP protein would be expressed either in its native form or as a fusion protein containing the CBP-tag on its carboxy terminus. In both cases, cloning was accomplished using Stratagene's Seamless™ cloning kit (Padgett, K. A. et al., *Strategies* 9:14–16 (1996), herein incorporated by reference) to amplify the GFP gene from the original TU58 template (Chalfie, M. et al. *Science* 263:802–805 (1994)). PCR was conducted with the high-fidelity Pfu polymerase and with primers that contained the Eam recognition site.

For each reaction, 0.01 pmol TU58 DNA template was combined with 8 pmol of each PCR primer (Table 1, Oligo Nos. 19F/19R or 19F/20) in a 50 µl reaction volume containing 200 µM of each deoxynucleotide (dNTP), 2.5 units cloned Pfu DNA polymerase in 1× cloned Pfu buffer. The reactions were amplified once at 94° C. for 3 min/54° C. for 1 min/72° C. for 1 min. with 9 subsequent cycles of 45 sec/45 sec/1 min, respectively. Each reaction was then supplemented with 50 µl containing 200 µM each dATP, dTTP, 0.5 mM 5-methyl-dCTP (Pharmacia), 1.25 units cloned Pfu DNA polymerase in 1× cloned Pfu buffer and amplified an additional 5 rounds at 95° C. for 50 sec/54° C. for 40 sec/72° C. for 1 min.

The PCR products were pooled, phenol:chloroform extracted and precipitated. The precipitated DNA pellet was resuspended in 50 µl TE (5 mM Tris Buffer: 1 mM EDTA) and 5 µl were digested with 24U Eam1104I (Stratagene) and 1× Uni buffer in a total volume of 50 µl. pdual 2800-9.12 vector (1.2 µg) (having unmodified polyA and CMV promoter sites) was cut with Eam1104I exactly as described by the manufacturer. Both reactions were incubated overnight at 37° C. The digested vector and insert were ligated overnight at 16° C. in the presence of Eam1104I restriction enzyme, eliminating the need for gel purification of the restriction fragments. One hundred µl of XL-1 Blue MRF Supercompetent cells (Stratagene) were transformed with 2 µl of the ligation reaction. The resulting transformant were screened by PCR for the presence of the GFP gene. The construction created clones that expressed the GFP protein either with (Clone # 2833-7.11) or without (Construct 2800-47.3) the CBP fusion tag.

EXAMPLE IIB

Insertion of the GFP Reporter Gene into Dual Vectors with a Mutagenized CMV Promoter The GFP gene was cloned into clone #2995-71AgM-3, the final pdual vector, or clone #2995-71Rh-3, essentially as described above with the following changes. TU58 template was amplified with primer set 19F/20 and native Pfu polymerase (Stratagene) in the absence of methyl dCTP for total of 21 rounds, because the GFP does not contain any internal Eam sites. The GFP PCR product was digested with Eam1104I for 2 h at 37° C. in the presence of 100 µg/ml BSA. The vector was digested o/n in the presence of 1×BSA and gel purified using the QiaQuick (Qiagen) gel purification kit. One hundred µl of XL1-Blue (Stratagene) Supercompetent cells were transformed with 5 µl of the ligation reaction. Colonies were screened by PCR for clones that contained the GFP insert. This construction created clones that expressed the GFP-CBP fusion protein. Clone # KP 2995-87.6 (CMV-AgM mutant) and Clone # KP 2995-87.27 (CMV-Rh mutant) were used to study protein expression in prokaryotic and eukaryotic cells (Table 2).

EXAMPLE III

Constitutive Expression of GFP and GFP-CBP Fusion Proteins in BL21(DE3) Bacterial Cells In order to evaluate the hybrid T7/lacO promoter in prokaryotic cells, induction studies of CBP-tagged (KP2833-7.11) and untagged (KP2800-47.3) GFP proteins were performed using Clone Nos. KP2800-47.3 and KP2833-7.11, which were derived from the original, unmodified vector Clone No. 2800-9.12, in the two indicator cell strains BL21(DE3) and BL21(DE3)pLysS, as well as in BL21 cells which do not contain the T7 RNA polymerase. The expression levels of the CBP-tagged and untagged GFP clones were examined in prokaryotic cells and compared to each other, as well as to the original clone TU58 (Chalfie, M. et al., *Science* 263:802–805 (1994)) which features the GFP gene in a pET3 vector backbone. Expression levels of untagged GFP were found to be approximately the same in pdual and pET3. The GFP-CBP fusion protein, however, appeared to be expressed approximately 3–5 fold less compared to the untagged protein.

The induction profiles indicated that the cells contained almost the same amount of protein, whether or not they were grown in the presence or absence of IPTG, suggesting either that the hybrid T7/lacO promoter was not repressed efficiently, or that constitutive transcription was originating from another vector promoter.

Thus, the vector Clone Nos. 2800-9.12 and 2995-57.2 may be employed to mediate constitutive expression of a gene of interest in a prokaryotic cell, as long as the gene of interest encodes a non toxic gene product.

EXAMPLE IVA

Ability of the Vectors of the Invention to Express a Gene Transiently in Mammalian Cells Although GFP is not toxic to most organisms, including mammalian cells, the possibility existed that a GFP-CBP fusion protein could not be expressed in mammalian cells. Because there are many calmodulin-regulated proteins in mammalian cells, the expression of high-levels of a protein that features a calmodulin binding peptide tag could potentially sequester cellular calmodulin necessary for normal intracellular signaling in such cells and, as such, be detrimental to the cells. To test this hypothesis, the constructs of Example IIA where transfected into NIH 3T3 cells, CHO cells, Cos cells and Hela cells, as described above. Transfected cells were visualized with a fluorescent microscope using the FITC filter cube.

The transfected cells were incubated in fresh DMEM+ medium at 28–30° C. for 6 hr. to allow maturation of the green fluorescent protein (GFP). The cells were then washed twice with sterile PBS, overlaid with 1–2 ml of PBS and magnified using a 20× objective. The cells were visualized on a phase contrast fluorescent microscope (Nikon) equipped with a 100 watt mercury lamp and an FITC filter cube of excitation and emission frequencies of 470 nm and 510 nm, respectively. The fluorescent cells were photographed using Ektachrome 400-speed slide film.

Although no fluorescence was evident in the transfected NIH 3T3 cells, possibly due to poor transfection efficiency, fluorescent cells were present in the other three cell lines regardless of whether the CBP tag was expressed. These results indicated that the CBP tag had no detrimental effects on the CHO cells, Cos cells and Hela cells when expressed transiently.

Immunodetection (see western methods below in Example IVB) of the GFP-CBP fusion protein and the untagged GFP from transiently transfected CHO cells lysates showed that, when total protein content was normalized, expression of untagged GFP was slightly higher than CBP-tagged GFP. Data generated with the ZERO-Dscan densitometry program of the Eagle Eye II Still Video System showed that the expression of GFP alone was approximately 2-fold higher compared to the GFP-CBP fusion protein.

EXAMPLE IVB

Ability of the Vectors of the Invention to Express a Gene Stably in Mammalian Cells To determine if stable mammalian cell lines could be generated with the dual vector, CHO cells were transfected with the constructs of Example IIA. G418 (Life Technologies) was then applied to the growth medium of the transfected CHO cells at a concentration of 1.5 mg/ml. The G418 concentrations had previously been established from acute toxicity studies performed on these cells. After culturing the cells for approximately 2 weeks in G418 selection medium, single clones were isolated, transferred to fresh plates and grown in the selection medium until confluent. Stable cells lines were frozen in 95% FBS/5% DMSO and assayed for GFP expression by standard fluorescent microscopy and western analysis.

None of the eukaryotic clones exhibited fluorescence with standard fluorescent microscopy. However, this result was not unexpected since GFP lacks enzymatic activity, and thus relatively high levels of GFP are needed to visualize a fluorescent signal in cells (Cubitt, A. B. et al., *TIBS* 20:448–455 (1995); Rizzuto, R. et al., *Curr. Biol.* 5:635–642 (1995). Moreover, heat has been shown to cause improper fluorophore formation (Lim, C. R. et al., *J. Biochem. (Tokyo)* 118:13–17 (1995)), and it is likely that the temperature for optimum cell growth (37° C.) resulted in incorrect protein folding and therefore reduced fluorescence below the threshold of visibility. The stable CHO cell lines did, however, exhibit expression of GFP by western analysis with a commercially available polyclonal GFP Antibody.

Western analysis was performed on lysates of transiently transfected CHO cells (Example IVA) and stable GFP-expressing CHO cell lines. Lysates were prepared as follows: 6 well plates or 60 mm culture dishes containing a monolayer of cells were washed twice with 1× phosphate buffered saline (PBS). 1 ml of PBS was applied to the plate and the cells were scraped off the dish with a sterile cell scraper. The cells were transferred to a 1.5 ml microfuge tube and pelleted for 5 min. at 5000 rpm at 4° C. The supernatant was removed via aspiration, the cell pellet was resuspended in 100 μl ice-cold lysis buffer (25 mM Tris pH 8, 1 mM EDTA, 1 mM EGTA) was vortexed thoroughly. The resuspended cells were frozen in liquid nitrogen and immediately thawed at 37° C. This freeze/thaw cycle was repeated twice. The solution was then homogenized with a $25^{5/8}$-gauge syringe (repeated 10–15 times) to shear the genomic DNA. The lysate was centrifuged for 2 min. at 13000 rpm at 4° C. to remove any remaining cell debris.

Approximately 10 μg of total protein were loaded per lane on a 4–20% Tris-glycine SDS polyacrylamide gel. The proteins were fractionated into discrete bands and electroblotted onto a nitrocellulose membrane. The GFP protein was visualized either by chromogenic method using commercially available GFP antiserum, streptavidin conjugated secondary and BCIP/NBT for visualization, or by chemiluminescence using commercially available GFP antiserum and horseradish peroxidase (HRP) conjugated secondary antibody. Both methods are described below in more detail. The mammalian cell lysates transfected with GFP constructs were found to contain a single band that migrated at the position expected for GFP. The results of these experiments thus confirm that the pdual vector is able to direct expression of both GFP and GFP-CBP in mammalian cells.

Western analysis of eukaryotic cells was performed as follows: Eukaryotic cell lysates containing 10 μg of total protein were brought up to 20 μl with 1×PBS/1%SDS, combined with 5 μl of 5× Laemmli buffer and boiled for 3 min. The samples were centrifuged briefly to collect any condensate, loaded onto a 4–20% Tris-glycine polyacrylamide gel (Novex) and electrophoresed for 1.5 h at 125 volts with SDS running buffer (12 mM Tris-HCl pH 8.3, 96 mM Glycine, 1% (v/v) SDS). The protein was transferred to Nitrocellulose for 1.5–2 h at 200–250 mA using 1× transfer buffer (12 mM Tris-HCl pH 8.3, 96 mM Glycine, 20% (v/v) Methanol). The blot was subsequently incubated in blocking buffer (5% nonfat dry milk in 1×Tris-buffered saline (TBS)) overnight at 4° C. The polyclonal primary GFP-antibody (primary Ab) was diluted 1:2000 in blocking buffer that contained 0.1% Tween-20 and the membrane was incubated in the antibody solution for 1 h at RT (or overnight at 4° C.). The membrane was subsequently washed for 30–40 min. with 5 changes of 1X TBS/0.1% Tween-20 (TBS-T) buffer and incubated for 1 h at RT with HRP-conjugated goat-anti-rabbit antibody (secondary Ab). The secondary Ab was diluted 1:30,000 in blocking buffer/Tween-20 which also included Streptavidin-HRP at a 1:4000 fold dilution, to visualize the biotinylated protein standard (Sigma). The membrane was then washed 30–40 min. with 5 changes of 1× TBS-T and immersed for 1 min. in 20 ml ECL western developing solution (Amersham) or Western View (Transduction Laboratories) developing solution. The protein bands were visualized by exposure of the membrane to BioMax film for 5–10 sec up to 5 min.

Western detection using the chromogenic method of BCIP/NBT were incubated for a minimum of 2 h in blocking solution made with 1×TSA (50 mM Tris-HCl, pH 7.4, 0.9% NaCl, 0.1% Sodium azide) and 5% nonfat dry milk. The primary Ab was the same as described above, the secondary Ab was alkaline-phosphatase (AP)-conjugated goat anti rabbit antibody. Each antibody was diluted 1:2000 in blocking buffer. The blot was incubated in the primary Ab solution for 1 h at room temperature (or overnight at 4° C.). The membrane was then washed with 1×TSA for 0.5–1 h with 4 changes of buffer before and after incubation with the (AP)-conjugated secondary Ab for 2 h at room temperature. The membrane was again washed as described above and briefly equilibrated in 1× TNM (100 mM Tris pH 9.5, 100 mM NaCl, 50 mM MgCl$_2$) buffer before the BCP/NBT developing solution (30 μl BCIP/40 μl NBT per 10 ml TNM) was applied. The blot was allowed to develop from 1–10 min. in the dark before the reaction was stopped with 20 mM Tris pH 2.9 and the bands were visualized.

EXAMPLE V

Identification of a Bacterial Transcription Start Site When the T7/lacO Promoter is Repressed Since protein expression was observed in BL21 bacterial cells (which do not contain a T7 RNA polymerase), it appeared that the T7/lacO hybrid promoter might not be involved in producing the high background expression, but rather that transcription might be initiated at another promoter.

To investigate the possibility that the CMV promoter, which is located upstream of the hybrid phage promoter, might contain a cryptic transcription initiation signal that was recognized by the bacterial RNA polymerase, primer extension assays of bacterial RNA templates, using AMV reverse transcriptase, were conducted.

For such assay, approximately $5 \times 10^4$ to $1 \times 10^5$ cpm of $^{32}$P labeled 24-mer (Oligo No. 18, Table 1) was hybridized to 6–10 μg of RNA in the presence of 150 mM KCI, 10 mM Tris-HCl, pH 8 and 1 mM EDTA. The reaction was first heated to 90° C. for 2 min. and then incubated at 55° C. for 30 min. The reaction was centrifuged briefly at 4° C. to collect any condensate and immediately stored on ice. The annealed RNA/primer mixture was brought up to 29 μl with 10.7 μl water, 0.3 μl Actinomycin D and 3 μl of 10× reverse transcription buffer (450 mM Tris, pH 8, 60 mM MgCl$_2$, 50 mM DTT, 5 mM of each dNTP), then 1 μl of AMV reverse transcriptase (RT) was added and the reaction was incubated at 45° C. for 1 h. Subsequently 1 μl of 0.5 M EDTA, pH 8 was added to stop the RT reaction and the RNA was digested for 30 min. at 37° C. with 1 μl of RNace-It cocktail. The reaction was extracted once with phenol/chloroform/isoamyl alcohol and the cDNA was precipitated from the aqueous phase with 0.1 volumes 10× STE and 2.5 volumes of 100% ethanol for 2 h at −20° C. The cDNA was collected by centrifugation at 13 k for 15 min. in a cold microcentrifuge. The pellet was briefly dried in-vacuo and resuspended in 2 μl TE and 2 μl of formamide were added to the dissolved cDNA. The resuspended cDNA was then heated 3 min. at 85° C. and 2 μl were loaded onto a 6% CastAway gel.

These assays revealed that transcription in prokaryotes was initiating within the CMV promoter. The transcription start site was mapped to the nucleotide immediately preceding the CMV TATA box (FIG. 3). Evaluation of the sequence surrounding the transcription initiation site revealed a strong resemblance to the −35 and −10 consensus regions that are present in most bacterial promoters (Hawley, D. K. et al., *Nucl. Acids Res.* 11:2237–2255 (1983)). Indeed, the 5 most strongly conserved nucleotides of the 7 bases that represent the −35 consensus sequence and the 3 most highly conserved nucleotides of the −10 consensus site were also present here (FIG. 3).

To eliminate transcription from this cryptic promoter several nucleotides near the TATA region were mutagenized. Sequence information from Cytomegaloviruses that infect African green monkeys (AgM) and Rhesus monkeys (Rh) was used to determine possible changes that might not affect eukaryotic transcription initiation in a negative way (e.g.: abolish transcription initiation). Both viruses showed divergence to different degrees in the region prior to the TATA box of their respective CMV immediate early promoters compared to that of human CMV (FIG. 3).

The original CMV promoter of the second pdual vector #2995-57.2 was then mutagenized to incorporate the sequence of either the AgM or Rh CMV immediate early promoter (FIG. 3), resulting in vector clones 2995-71-AgM-3 and 2995-71-Rh-3. Construction of clones that contain the GFP reporter in these modified vectors is described in Example IIB.

EXAMPLE VI

Inducible Expression of GFP-CBP Fusion Protein in BL21(DE3) Cells

In order to demonstrate that the mutations in the CMV promotor allowed the hybrid T7/lacO phage promoter to mediate inducible expression of a gene in a prokaryotic cell, the IPTG induction studies were repeated. Induction profile comparisons of the original GFP Clone No. 2833-7.11 (Example IIA and Table 2) and the mutagenized CMV clones (Example IIB and Table 2) No. 2995-87.6 (featuring the AgM mutation) and No. 2995-87.27 (featuring the Rh mutation) were performed.

In such studies, single BL21(DE3) and BL21 bacterial colonies containing the above constructs were grown overnight at 37° C. in 3 ml NZY broth supplemented with 50 µg/ml kanamycin (NZY/kan). A portion of the culture was diluted 20-fold into 10 ml of the same medium. Each culture was grown until an $OD_{600}$ of 0.6–0.8 was reached. Two 1 ml samples were removed from each culture and IPTG (Stratagene) was added to a final concentration of 200 µM, the control received no IPTG. The samples were allowed to grow for an additional 3–4 h at 37° C. Cells were transferred to microcentrifuge tubes and harvested by centrifuging at 4° C. for 5 min. at 5000 rpm. The cell pellets were resuspended in 0.5–1 ml ice-cold lysis buffer (100 mM NaCl, 50 mM Tris pH8, 100 mM EDTA, 1 mM DTT) and sonicated on ice at 20% output for 30 seconds, which was repeated twice. The lysates were cleared of any remaining cell debris with a brief centrifugation step at 4° C. in a microcentrifuge (2–3 min. @ 13K) (see Sambrook, J., et al. (In: *Molecular Cloning, A Laboratory Manual*, Second Edition, Cold Spring Harbor Laboratories, Cold Spring Harbor, N.Y. (1989)). The total protein concentration was determined by Bradford assay. Equal amounts of protein from IPTG induced and uninduced bacterial lysates were resolved by SDS PAGE, transferred to nitrocellulose and visualized by chemiluminescence using GFP antiserum (see western protocol in Example IVB).

A strong induction profile was obtained. Both mutagenized versions of the pdual expression vector showed highly reduced GFP expression in uninduced BL21(DE3) cells compared to the nonmutagenized version. IPTG-treated BL21(DE3) cells on the other hand exhibited a dramatic increase in expression of GFP-CBP fusion protein. Clone No. 2995-87.6 showed no expression of GFP in the absence of T7 RNA polymerase, indicating that the AgM CMV mutations were more effective than the Rh CMV mutations in eliminating bacterial transcription initiation within the CMV promoter.

Although transcription was not completely abolished in repressed BL21(DE3) cells, it was reduced to extremely low, nearly undetectable levels. This result is consistent with the known fact that BL2(DE3) cells show a low basal degree of transcription in the repressed state. If desired, the level of basal expression can be reduced further by employing BL21(DE3)/pLysS cells (Stratagene) harboring the pLysS plasmid that encodes T7 lysozyme, a natural inhibitor of T7 RNA polymerase.

Alternatively, for a more rapid, but less rigorous, test of expression, BL21(DE3) cells, transformed with the GFP Clone No. 2995-87.6 vector, were grown at 30° C. for 24 h on an NZY plate containing kanamycin and IPTG. The colonies were photographed in the dark, using a long-wave UV light source. Colonies were observed that exhibited fluorescence, and hence GFP expression.

EXAMPLE VII

Mammalian Expression of GFP-CBP Fusion Protein

The constructs of Example IIB were also tested in CHO and Hela cells and compared to the original, unmutated GFP construct # 2833-7.11, to show that the mutated CMV promoters were still active in mammalian cells.

Both mutated promoters of clones 2995-87.6 (AgM) and 2995-87.27 (Rh) were able to initiate transcription in eukaryotic cells. Fluorescence microscopy showed brighter fluorescence in cells containing the mutated CMV promoter constructs compared to cells that harbored the clone with the original, unmutated CMV promoter (#2833-7.11). In fact, immunodetection with GFP antiserum and subsequent densitometry measurements supported the difference in fluorescence intensity observed during microscopy, and showed that protein expression was several fold higher in cells transfected with GFP constructs that contained the mutated versions of the CMV promoter.

EXAMPLE VIII

CBP-Affinity-Tag Protein Purification

As described above, a preferred vector of the present invention permits the expression of a protein of interest as a cleavable fusion with a ligand protein (such as calmodulin binding protein (CBP)). A CBP fusion protein can be cleaved by treatment with thrombin to release the protein of interest.

To demonstrate this, BL2(DE3) cells containing the clone GFP Clone No. 2995-87.6 were grown as described above. The presence of the CBP-tagged GFP fusion protein in bacterial-and mammalian cell lysates was further confirmed using the CBP detection kit (Stratagene). The GFP-CBP fusion protein was purified from bacterial cell lysates using the Affinity™ purification system (Stratagene). The purification was performed using the batch method described in the manual supplied with the kit. The calmodulin affinity resin with adsorbed GFP-CBP fusion protein was applied to a disposable column, washed and then eluted at neutral pH as specified in the manual. In detail, 10 ml of LB/kan broth was inoculated with a single colony of BL21(DE3) bacterial cells harboring plasmid Clone No. 2992-87.6 and grown overnight at 37° C. in a 50 ml conical tube with shaking. 1 L of LB/kan broth contained in a 2 L Erlenmeyer flask was inoculated with the overnight culture and grown until the bacteria reached an $OD_{600}$ of 0.6. Thereafter, 10 ml of the culture was removed to a 50 ml sterile conical tube and the remainder was induced with IPTG at a final concentration of 0.2 mM. Both induced and uninduced cultures were grown at room temperature for an additional 4 h before cells were harvested. The bacterial cells were centrifuged for 5 min. at 5000 rpm in a Beckman J-6B centrifuge at 4° C. The cell pellets were resuspended in ice-cold lysis buffer (50 mM Tris-HCl, pH 7.5, 150 mM NaCl, 10 mM β-mercaptoethanol, 1 mM Mg-acetate, 1 mM imidazol) containing 2 mM $CaCl_2$. Lysozyme (Sigma) was added to the slurry to a final concentration of 0.2 mg/ml and the solution was incubated on a rotary shaker for 30 min. at 4° C. The cell slurry was then sonicated with a micro probe at setting 4, for 30 sec while kept on ice continuously. This was repeated 5 times with 2–3 min. rest periods between sonication bursts. The cell lysate was cleared of any cell debris by centrifugation at 15,000 rpm for 15 min. at 4° C. in a Sorvall SS34 rotor.

Purification of the GFP/CBP fusion protein was performed according to the protocol supplied with the Affinity™ protein purification kit. One half (15 ml) of the IPTG induced, cleared cell lysate was incubated with 2 ml of Calmodulin-Sepharose (CaM) resin for 2 h at 4° C. on a rotary shaker. The GFP-adsorbed CaM resin was then loaded onto a disposable chromatography column (Bio-Rad). The resin containing column was washed twice with 15 ml ice-cold lysis buffer containing 2 mM $CaCl_2$ and 0.1 mM $CaCl_2$, respectively. The GFP fusion protein was eluted with 10 ml ice-cold lysis buffer containing 2 mM EGTA, followed by 10 ml ice-cold lysis buffer containing 2 mM EGTA/1 M NaCl. The eluates were collected in 2 ml fractions and protein concentration was checked with Coomassie Plus protein assay reagent (Pierce) according to the manufacturer's protocol. The fractions were combined and concentrated approximately 8-fold in a microcon-3 spin column.

Aliquots of the bacterial lysate and the eluted fraction containing the fusion protein were resolved by SDS PAGE and visualized by Coomassie staining. Commercially available recombinant GFP protein was used for size comparison. The size of the GFP-CBP hybrid protein is approximately 32 kD, compared to the untagged 28 kD GFP. The results confirmed that the small CBP affinity tag, located on the C-terminus of the protein, provided an effective and convenient way to purify the protein of interest from bacteria. In addition, the thrombin protease cleavage site allows cleavage to occur in the presence of thrombin, for applications where the removal of the affinity tag is desired. Such cleavage was achieved when the purified GFP-CBP fusion protein was incubated with 2 μg of thrombin in a 100 μl total reaction volume, in the presence of 2 mM $Ca_2$. The digest was incubated at room temperature and 25 μl fractions were removed at time points 0 h, 1 h, 6 h, 24 h and frozen in the presence of 1× Laemmli buffer until all time points were collected. Fifty percent cleavage was observed at 6 h and 95 percent cleavage was achieved at 24 h.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features herein before set forth and as follows in the scope of the appended claims.

What is claimed is:

1. A dual expression vector, said vector comprising:
   (a) a cloning site;
   (b) a first transcription element comprising a prokaryotic promoter and a second transcription element comprising a eukaryotic promoter, sufficient to permit transcription of a polynucleotide inserted into said cloning site in both a prokaryotic and a eukaryotic cell,
   (c) translation elements comprising a Kozak consensus sequence, sufficient to permit translation of an RNA transcript of said polynucleotide in both a prokaryotic and a eukaryotic cell; and
   (d) elements sufficient to permit the replication of said vector in prokaryotic cells, wherein said vector mediates the expression of said inserted polynucleotide in both a prokaryotic and a eukaryotic cell, wherein said vector is pdual selected from the group consisting of Clone #2800-9.12, Clone #2995-57.2 and Clone #2995-71AgM-3.

* * * * *